US009212383B2

(12) United States Patent
Schofield

(10) Patent No.: US 9,212,383 B2
(45) Date of Patent: Dec. 15, 2015

(54) BIOLOGICAL DETECTION SYSTEM AND METHOD

(75) Inventor: David Alexander Schofield, Hollywood, SC (US)

(73) Assignee: GUILD ASSOCIATES, INC., Dublin, OH (US)

( * ) Notice: Subject to any disclaimer, the term of this patent is extended or adjusted under 35 U.S.C. 154(b) by 948 days.

(21) Appl. No.: 12/593,133

(22) PCT Filed: Apr. 4, 2008

(86) PCT No.: PCT/US2008/059465

§ 371 (c)(1), (2), (4) Date: Sep. 25, 2009

(87) PCT Pub. No.: WO2009/005869

PCT Pub. Date: Jan. 8, 2009

(65) Prior Publication Data

US 2010/0285460 A1 Nov. 11, 2010

Related U.S. Application Data

(60) Provisional application No. 60/910,168, filed on Apr. 4, 2007.

(51) Int. Cl.

*C12Q 1/04* (2006.01)
*C12Q 1/66* (2006.01)

(Continued)

(52) U.S. Cl.

CPC .............. *C12Q 1/04* (2013.01); *C12N 15/1086* (2013.01); *C12Q 1/66* (2013.01); *G01N 33/569* (2013.01);

(Continued)

(58) Field of Classification Search

None

See application file for complete search history.

(56) References Cited

U.S. PATENT DOCUMENTS

| | | | |
|---|---|---|---|
| 4,861,709 A | 8/1989 | Ulitzur et al. | 435/6 |
| 5,187,061 A | 2/1993 | Gutterson et al. | 435/5 |

(Continued)

FOREIGN PATENT DOCUMENTS

| | | |
|---|---|---|
| WO | 99/45354 | 9/1999 |
| WO | 2006/092629 | 9/2006 |

OTHER PUBLICATIONS

Thouand, G. et al. Journal of Food Protection 71(2):380-385 (Feb. 2008).*

(Continued)

*Primary Examiner* — Diana B Johannsen

(74) *Attorney, Agent, or Firm* — Baker Botts L.L.P.

(57) ABSTRACT

The present disclosure, according to some embodiments, relates to phage-based biological detection systems, compositions, and methods. In some embodiments, it relates to a detection system and method using phage binding and bacterial infection to detect the presence of a target molecule (e.g., a toxin). One detection system may include a genetically engineered phage that expresses a surface molecule able to bind a target molecule and/or target microorganism; a bacterium susceptible to infection by the phage; and a detection component able to determine whether the bacterium has been infected by the phage. Infection of a bacterium by a phage may be indicative of phage binding to the target molecule and/or target microorganism. One method may include placing a sample suspected of containing the target molecule and/or target microorganism with a binder; adding a genetically engineered phage having reporter genetic material and able to bind the target molecule and/or target microorganism; washing away unbound phage; releasing phage bound to the target molecule and/or target microorganism; infecting a bacterium with the released phage; and detecting the presence of any reporter genetic material in the bacterium. Reporter material in the bacterium may correlate with target molecule and/or target microorganism in the sample. In some embodiments, the disclosure relates to a detection system and method using phage comprising a reporter to infect a microorganism (e.g., *Bacillus anthracis*), wherein the reporter is selectively (e.g., only) detectable upon phage infection.

28 Claims, 13 Drawing Sheets

(51) Int. Cl.
*C12N 15/10* (2006.01)
*G01N 33/569* (2006.01)

(52) U.S. Cl.
CPC *G01N 33/56983* (2013.01); *C12N 2795/00011* (2013.01); *C12N 2795/10311* (2013.01); *C12N 2795/14111* (2013.01); *G01N 2333/32* (2013.01)

(56) References Cited

U.S. PATENT DOCUMENTS

| | | | | |
|---|---|---|---|---|
| 5,498,525 | A | 3/1996 | Rees et al. | 435/29 |
| 5,824,468 | A | 10/1998 | Scherer et al. | 435/5 |
| 5,888,725 | A | 3/1999 | Sanders | 435/5 |
| 5,914,240 | A | 6/1999 | Sanders | 435/7.32 |
| 6,300,061 | B1 | 10/2001 | Jacobs, Jr. et al. | 435/6 |
| 6,395,504 | B1 | 5/2002 | Trudil | 435/29 |
| 6,544,729 | B2 | 4/2003 | Sayler et al. | 435/5 |
| 6,555,312 | B1 | 4/2003 | Nakayama | 435/5 |
| 6,660,470 | B1 | 12/2003 | Sanders | 435/5 |
| 7,166,425 | B2 | 1/2007 | Madonna et al. | 435/5 |
| 7,244,612 | B2 | 7/2007 | Goodridge | 435/306.1 |
| 7,276,332 | B2 | 10/2007 | Goodridge | 435/4 |
| 2004/0137430 | A1 | 7/2004 | Anderson et al. | 435/5 |
| 2004/0191859 | A1 | 9/2004 | Tabacco et al. | 435/69.1 |
| 2005/0003346 | A1 | 1/2005 | Voorhees et al. | 435/5 |
| 2005/0118567 | A1 | 6/2005 | Merril et al. | 435/5 |
| 2007/0059725 | A1 | 3/2007 | Voorhees | 435/6 |
| 2007/0072174 | A1 * | 3/2007 | Sayler et al. | 435/5 |
| 2008/0193418 | A1 | 8/2008 | Walter | 424/93.6 |
| 2008/0193917 | A1 | 8/2008 | Schofield et al. | 435/5 |
| 2009/0068638 | A1 | 3/2009 | Shabani et al. | 435/5 |
| 2009/0117536 | A1 | 5/2009 | Mattey et al. | 435/5 |
| 2009/0155768 | A1 | 6/2009 | Scholl et al. | 435/5 |
| 2009/0246752 | A1 | 10/2009 | Voorhees et al. | 435/5 |

OTHER PUBLICATIONS

Chan, P.F. et al. Journal of Bacteriology 185(6):2051-2058 (Mar. 2003).*
Fujinami, Y. et al. Journal of Health Science 50(2):126-132 (2004).*
Schofield, D.A. and Westwater, C. Journal of Applied Microbiology 107:1468 (2009).*
Schofield, D.A. et al. Journal of Microbiological Methods 95:156 (2013).*
European Patent Office Communication for EP Application No. 08 826 012.0 dated Feb. 10, 2010, 5 pages.
Billard et al., "Bioluminescence-Based Assays for Detection and Characterization of Bacteria and Chemicals in Clinical Laboratories", Clinical Biochemistry, vol. 31, dated Feb. 1998, pp. 1-14.
Hindson et al.; "Autonomous Detection of Aerosolized Biological Agents by Multiplexed Immunoassay With Polymerase Chain Reaction Confirmation"; Anal. Chem., 77; pp. 284-289, 2005.
Schofield et al.; "Doc-mediated cell killing in *Shigella flexneri* using a Cl/LacI controlled expression system"; FEMS Microbiology Letters, 215; pp. 237-242, 2002.
Greenfield et al.; "Microbiological, Biological, and Chemical Weapons of Warfare and Terrorism"; Am J Med Sci, 323(6); pp. 326-340, 2002.
Koch et al.; "Optical flow-cell multichannel immunosensor for the detection of biological warfare agents"; Biosensors & Bioelectronics, 14; pp. 779-784, 2000.
Goldman et al.; "Phage-displayed peptides as biosensors reagents"; J. Mol. Recognit., 13; pp. 382-387, 2000.
Malmborg et al.; "Selective Phage Infected Mediated by Epitope Expression on F Pilus"; J. Mol. Biol., 273; pp. 544-551, 1997.
Wright et al.; "Hypersymmetry in a transcriptional terminator of Escherichia coli confers increased efficiency as well as bidirectionality"; The EMBO Journal, vol. 1; pp. 1957-1964, 1992.
International Preliminary Report on Patentability; PCT/US2008/059465; pp. 12, Oct. 15, 2009.
Reiman et al.; "Indirect detection of *Bacillus anthracis* using real-time PCR to detect amplified gamma phage DNA"; Journal of Microbiological Methods; vol. 68; pp. 651-653, 2007.
Schuch et al.; "Detailed Genomic Analysis of the Wβ and γ Phages Infecting *Bacillus anthracis:* Implications for Evolution of Environmental Fitness and Antibiotic Resistance"; Journal of Bacteriology, vol. 188, No. 8; pp. 3037-3051, Apr. 2006.
Abshire et al.; "Production of Validation of the Use of Gamma Phage for Identification of *Bacillus anthracis*"; Journal of Clinical Microbiology, vol. 43, No. 9; pp. 4780-4788, Sep. 2005.
European Office Action; Application No. 08 826 012.0-1233; pp. 6, Aug. 9, 2010.

* cited by examiner

BIOLOGICAL DETECTION SYSTEM AND METHOD

CROSS REFERENCE TO RELATED APPLICATION

This application is a U.S. national stage application of International Application No. PCT/US2008/059465 filed Apr. 4, 2008, which designates the United States of America, and claims the benefit of U.S. Provisional Patent Application Ser. No. 60/910,168, filed Apr. 4, 2007. The contents of the foregoing applications are hereby incorporated in their entirety by reference.

TECHNICAL FIELD

The present disclosure, according to some embodiments, relates to a biological detection system and method. In a more specific embodiment it relates to a detection system and method using phage binding and bacterial infection to detect the presence of a target microorganism (e.g., *Bacillus anthracis*).

BACKGROUND

Toxins may be identified using mouse bioassays, in which toxin specific antibodies protect the mice against the lethal action of the toxin. These bioassays, although very sensitive, may take 1-4 days to complete and require animal testing. Other types of toxin (e.g., seafood toxins) detection methods may require expensive laboratory equipment (mass spectrometry) and expertise for use and may not be suitable for use in nonlaboratory environments.

Newer detection and identification methodologies include polymerase chain reaction (PCR) assays and immunoassays. PCR assays are very specific and sensitive due to the amplification process and theoretically, may detect as little as one target molecule; however, PCR assays generally require some target preparation, and are not useful for the detection of purified toxins since they lack the necessary genetic information.

SUMMARY

The present disclosure, in some embodiments, relates to phage-based compositions, methods, and systems for detecting and/or killing a microorganism (e.g., *Bacillus anthracis*). Detection may achieved by germinating spores, infecting cells with an engineered phage having a reporter (e.g., luxAB), and detecting the reporter. For example, in some embodiments, a detection system may comprise a phage having a reporter and operable to infect a *Bacillus* microorganism and a detector operable to detect the reporter. A *Bacillus* microorganism may include species and/or strains that comprise and/or produce a toxin (e.g., *Bacillus anthracia*).

A reporter may comprise, according to some embodiments, a reporter nucleic acid. A reporter nucleic acid may become detectable upon infection of the *Bacillus* microorganism, in some embodiments. For example, a reporter nucleic acid may comprise one or more luxAB reporter genes and a detector may comprise a bioluminescence detector. A phage, in some embodiments may comprise a non-lytic phage and/or a lytic phage. For example, a phage may comprise Wβ and/or γ.

According to some embodiments, a method of detecting the presence of a *Bacillus* microorganism in a test sample may comprise contacting the test sample with a phage configured and arranged to infect the *Bacillus* microorganism under conditions that permit the infection. A phage may comprise a reporter that is and/or becomes detectable only upon or after infection. A method may further comprise detecting the reporter, wherein detection of the reporter may be indicative of presence of the *Bacillus* microorganism in the sample, while non-detection of the reporter may be indicative of absence of the *Bacillus* microorganism in the sample. In some embodiments, detecting infection of the *Bacillus* may further comprise detecting lysis of the *Bacillus* and/or detecting progeny phage.

In some embodiments, a kit for detecting a *Bacillus* microorganism may comprise a genetically engineered phage operable to infect a *Bacillus* microorganism, wherein the phage comprises a reporter that is detectable only upon or after infection, a detector, and one or more containers for contacting the phage with a sample. A kit may further include sample collection containers and/or materials.

In some embodiments, the present disclosure also relates to phage-based compositions, methods, and systems for detecting a molecule and/or cell of interest. Detection may be achieved by (1) contacting a sample (e.g., suspected of containing the target molecule and/or cell of interest) with a binder configured and arranged to bind the target molecule and/or cell of interest, if present, (2) contacting the mixture with a phage comprising (a) a reporter and (b) a surface molecule configured and arranged to bind the binder, (3) eluting bound phage, (4) contacting eluted phage with a host microorganism under conditions permitting phage infection of the host microorganism, (5) detecting the reporter, and (6) intermediate washing steps as desired and/or required. Detection may also be achieved, in some embodiments, by detecting a target molecule associated with (e.g., on the surface of or secreted by) the microorganism.

A detection system, according to some embodiments may comprise a phage comprising (a) a reporter and (b) a surface molecule, wherein the phage is configured and arranged to infect a host microorganism. A detection system may further comprise a binder configured and arranged to bind a target molecule and/or target microorganism to form a binder-target molecule complex and/or a binder-target microorganism complex, wherein the surface molecule is configured and arranged to selectively bind to the binder-target molecule complex and/or the binder-target microorganism complex. For example, a binder may be configured and arranged to bind a target molecule. A target molecule may be comprised in a microorganism, according to some embodiments. A target molecule to be detected may comprise, in some embodiments, an amino acid, a protein, a carbohydrate, a nucleic acid, a lipid, and combinations thereof. For example, a target molecule that may be desirably detected may comprise, without limitation, a Staphylococcal enterotoxin, a botulinum toxin, ricin, ϵ-toxin, and combinations thereof. Further examples may include pharmaceutical compounds (e.g., steroids). A target molecule may also be and/or comprise a portion of a larger molecule (e.g., a methyl group on a nucleic acid).

In some embodiments, a surface molecule may comprise a material selected from the group consisting of a protein (e.g., an antibody and/or an antibody fragment), a carbohydrate, a nucleic acid, a lipid, and combinations thereof. A phage surface molecule may have a binding affinity for the binder-target molecule complex and/or the binder-target microorganism complex of more than about $10^{-5}$ M and/or more than about $10^{-8}$ M. A detection system binder may comprise a material selected from the group consisting of a protein (e.g., an antibody and/or an antibody fragment), a carbohydrate, a nucleic acid, a lipid, and combinations thereof. A binder molecule may have a binding affinity for the target molecule and/or the target microorganism of more than about $10^{-5}$ M and/or more than about $10^{-8}$ M according to some embodiments. A reporter nucleic acid, in some embodiments, may comprise a luxAB reporter gene. A phage, in some embodiments may comprise a non-lytic phage and/or a lytic phage. For example, a phage may comprise M13.

In some embodiments, a method of detecting the presence of a target molecule in a test sample may comprise contacting a binder with a test sample to form a binder-test sample mixture under conditions that permit binder-target molecule binding to form a binder-target molecule complex, if the target molecule is present in the test sample and/or contacting the binder-test sample mixture with a phage comprising (a) a reporter genetic material (e.g., a luxAB reporter gene) and (b) a surface molecule to form a binder-sample-phage mixture, wherein the phage is configured and arranged to infect a host microorganism and the phage surface molecule is configured and arranged to selectively bind to the binder-target molecule complex. A method of detecting presence of a target molecule in a test sample may also comprise, according to some embodiments, washing the binder-sample-phage mixture under conditions that remove phage not bound to the binder-target molecule complex to form a washed binder-sample-phage mixture and/or treating the washed binder-sample-phage mixture to release phage bound to the binder-target molecule complex, if any, from the complex to form a released phage composition. In some embodiments, a method of detecting presence of a target molecule in a test sample may further comprise contacting the host microorganism with the released phage composition under conditions that permit uptake of at least a portion of the released phage, if present, by the host microorganism and/or detecting the presence of reporter genetic material in the host microorganism. Detecting the presence of reporter genetic material in the host microorganism may comprises detecting bioluminescence (e.g., of a bioluminescent protein produced only upon and/or after infection).

In some embodiments, a kit for detecting a target molecule and/or a target microorganism may comprise a phage comprising (a) a reporter and (b) a surface molecule, wherein the phage is configured and arranged to infect a host microorganism; a binder configured and arranged to bind a target molecule and/or target microorganism to form a binder-target molecule complex and/or a binder-target microorganism complex, wherein the surface molecule is configured and arranged to selectively bind to the binder-target molecule complex and/or the binder-target microorganism complex; and one or more containers configured and arranged to allow the binder and/or phage to be contacted with a test sample. A kit, in some embodiments, may further comprise a host bacterial cell.

BRIEF DESCRIPTION OF THE DRAWINGS

Some specific example embodiments of the disclosure may be understood by referring, in part, to the following description and the accompanying drawings, wherein.

Figure 1:
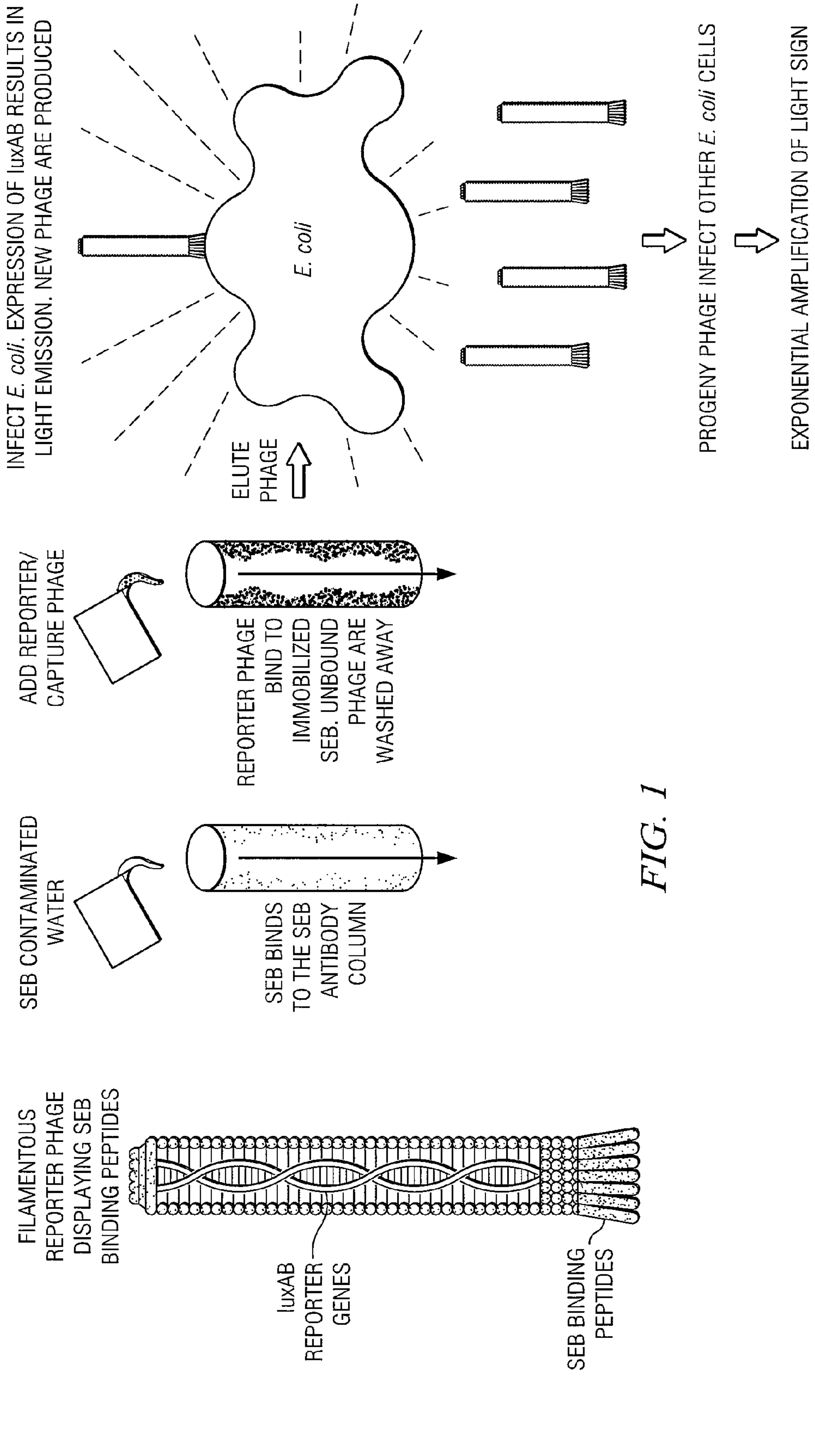
FIG. 1 is a schematic of a toxin detection system and method, according to a specific example embodiment of the present disclosure.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents.

DETAILED DESCRIPTION

Current biological detection methods may be expensive, time consuming and/or require expensive laboratory equipment and expertise. In addition, these detection methods may be limited in their sensitivity and require large amounts of the target material. Rapid and sensitive detection methodologies may contribute to saving lives and/or reducing costs. Some embodiments of the present disclosure relate a biological detection system and method.

For example, some embodiments relate to a detection system. The system may include a binder (e.g., an antibody) with a binding affinity for a target molecule and/or a target microorganism (e.g., $K_d \geq 10^{-5}$ M, $K_d \geq 10^{-6}$ M, $K_d \geq 10^{-7}$ M, $K_d \geq 10^{-8}$ M, or $K_d \geq 10^{-9}$ M). The system may also include a phage (e.g., a genetically engineered phage). A phage, in some embodiments, may comprise (e.g., express) a surface molecule having a binding affinity for a target molecule, a target microorganism, a target molecule-binder complex, and/or a target microorganism-binder complex (e.g., $K_d \geq 10^{-5}$ M, $K_d \geq 10^{-6}$ M, $K_d \geq 10^{-7}$ M, $K_d \geq 10^{-8}$ M, or $K_d \geq 10^{-9}$ M). The binding affinity of a surface molecule for a binder-target molecule complex and/or a binder-target cell complex may be higher (e.g., 10-fold higher, 100-fold higher, 1,000-fold higher, 10,000-fold higher, 100,000-fold higher, $10^6$-fold higher, and/or $10^7$-fold higher) than the binding affinity of the surface molecule for the unbound binder, target molecule, and/or target cell. According to some embodiments, a phage may include a reporter. A reporter may include, for example, a nucleic acid, which leads to the production of a detectable gene product (e.g., a bioluminescent protein) upon phage infection of a host cell (e.g., a bacterial cell).

The system may further include a composition formulated to permit binding of a target molecule and/or a target microorganism to a phage and/or binder. These compositions may be additionally formulated to solubilize phage that is not bound to a target molecule and/or a target microorganism and/or a binder. Thus, such compositions may be used to wash a binder and/or target molecule and/or a target microorganism to remove unbound phage. In some embodiments, a composition may be a phage wash composition formulated to permit binding of a phage surface molecule to a target molecule-binder complex and/or a target microorganism-binder complex, but solubilize, suspend, or otherwise separate surplus phage from the binder and/or target molecule. In other embodiments, a composition may be a release composition formulated to solubilize, suspend, or otherwise dissociate a phage from a binder. A target-molecule release composition may optionally be formulated to permit phage surface molecule-target molecule binding. A system may additionally include a host cell (e.g., a bacterium) capable of taking up at least a portion of a phage (e.g., a phage nucleic acid). In some embodiments, a cell may be susceptible to infection by a phage. A system may further include a detector configured to differentiate between cells that have taken up at least a portion of a phage and those that have not (e.g., phage-infected cells versus non-infected cells). Infection of a cell by a phage may be indicative of phage binding to the target molecule.

In another embodiment, the disclosure provides a method of detecting the presence of a target molecule. The method may include:

(a) contacting a binder with a sample comprising or possibly comprising a target molecule to form a binder-sample mixture under conditions that permit binder-target molecule binding (e.g., if the target molecule is indeed present);

(b) contacting the binder-sample mixture with a phage (e.g., a genetically engineered phage) having reporter genetic material, wherein the phage is capable of binding the target molecule (e.g., through a phage surface molecule); under conditions that permit phage-target molecule binding (e.g., if the target molecule is indeed present) to form a binder-sample-phage mixture, (c) washing the binder-sample-phage mixture under conditions that remove phage not bound to the target molecule from the binder (e.g., using a phage wash composition) to form a washed binder-sample-phage mixture;

(d) treating the washed binder-sample-phage mixture to release phage bound to the target molecule, if any, from the binder (e.g., by contacting the phage with a release composition) to form a released phage composition;

(e) contacting a bacterium with the released phage composition under conditions that permit uptake of at least a portion of the released phage, if present, by the bacterium (e.g., infection), and (f) detecting the presence of reporter genetic material (e.g., by detecting the production of a bioluminescent protein encoded by the reporter genetic material) in the bacterium.

The presence of reporter genetic material in the bacterium may be indicative of presence of a target molecule in the sample, while absence of reporter genetic material in the bacterium may be indicative of absence of the target molecule in the sample.

In some embodiments, a released phage composition may include one or more materials (e.g., detergents, solvents, salts) that may disfavor phage uptake by a bacterium and/or interfere with bacterial health and/or replication (collectively "interferant"). Accordingly, a phage release composition may be treated to reduce or remove at least a portion of the interferant(s) present, if any. Conditions that permit uptake of at least a portion of the released phage may include, according to some embodiments, pretreating or conditioning a released phage composition to have a desired composition, pH, ionic strength, temperature and/or other property to form a treated phage release composition.

In some embodiments, the detection system or method may be as sensitive as PCR. Without being limited to any particular mechanism of action, this sensitivity may be due, in whole or in part, to the possible amplification when phage expand in a single, infected bacterium and/or when a bacterium infected by a phage multiplies. In some embodiments, a detection system and/or method may be easily and/or rapidly adapted to detect any toxin of interest simply by changing the binding molecule (e.g., peptide, antibody, nucleic acid, or fragment thereof) on the cell surface of the phage and/or one or more binder components.

Systems, methods, and/or devices, according to some embodiments of the disclosure, may be configured to permit rapid detection of a target molecule and/or a target microorganism. For example, a target molecule may be detected in less than about twelve (12) hours, less than about ten (10) hours, less than about eight (8) hours, less than about six (6) hours, or less than about four hours. A target molecule may be detected in less than about three (3) hours, less than about two (2) hours, or less than about one (1) hour. The time required for detection may be a function of the time required for target binding, sample loading, washing, elution, infection, and/or reporter detection. For example, detection time may be reduced by electing to use columns, which permit reagents to flow through them, instead of plates, which may require more labor intensive manual application and removal of reagents.

Systems, methods, and/or devices, according to some embodiments of the disclosure, may be configured to permit sensitive detection of a target molecule. Sensitivity may be assessed in terms of the number of detectable eluted phage. For example, systems, methods, and/or devices of the disclosure may be configured to detect less than about five hundred (500) eluted phage, less than about one hundred (100) eluted phage, less than fifty (50) eluted phage, or less than twenty-five (25) eluted phage. In some specific examples, less than about ten (10) eluted phage or less than about five (5) eluted phage may be detected. In some embodiments, about $10^{-17}$ g of a target molecule (e.g., toxin) may be detected.

The present disclosure, according to some embodiments, relates to a biological detection system and method using phage binding and bacterial infection. Some embodiments relate to a detection system including a phage and a bacteria that may be infected by the phage. The phage may be genetically engineered to express a particular surface molecule. This surface molecule may be capable of binding to a target molecule under certain conditions, then being released from the target molecule under other conditions without destroying the phage's ability to infect the bacteria. In some embodiments, the surface molecule may include a peptide. In other embodiments, a surface molecule may include an antibody or antibody fragment. In still other embodiments, a surface molecule may include a carbohydrate, a nucleotide, and/or a lipid.

A system may also include a binder for the target molecule that binds the target molecule under conditions that also allow phage binding. The binder may be specific for the target molecule or non-specific. The binder may be unable to bind significant amounts of the phage without the target molecule. The system may have a washing component able to wash unbound phage from the binder and a release component which supplies the conditions for release of the phage from the binder. Additionally, the system may include a detection component able to determine if the bacteria have been infected by the phage and thus whether any target molecule was present on the binder. The detection component may be able to distinguish how many bacteria have been infected and, for this information, determine an amount of target molecule present on the binder. In some embodiments, the system may be so sensitive that the presence of a single target molecule or the infection of bacteria with a single phage may be detected. Thus, according to some embodiments, a system may exhibit the robust and easy to use nature of immunoassays but display the sensitivity of PCR.

The detection system may be provided as a kit. For example, the kit may contain at least a phage, a binder, and a bacteria. The kit may also be in the form of an automated portable light sensor device that may be used outside of a laboratory for the detection of a target molecule. Such a device may be particularly useful for detection of environmental toxins, for example in military situations, in suspected terrorist attacks, monitoring of local water and/or food supply, monitoring of disease outbreaks, or in suspected environmental or other disasters.

Phage may be resistant to environmental extremes and may be stored for months or years without a significant loss in phage infectivity. A bacteria, however, may loose its susceptibility to phage infection after storage for long periods of time. Some bacteria may regain their susceptibility to phage infection. Thus, the signal response time for bacteria may depend, in part, upon storage periods in kits and storage conditions.

The disclosure provides methods of detecting the presence of a target molecule and/or target microorganism. A sample suspected of containing a target molecule and/or target microorganism may be placed in conditions that allow binding of the target molecule and/or target microorganism to a binder. The binder may be specific to the target molecule and/or target microorganism or non-specific. The binder may be unable to bind appreciable amounts of phage in the absence of the target molecule and/or target microorganism. The binder may then be placed in the presence of a genetically engineered phage under conditions that allow continued binding of the target molecule and/or target microorganism to the binder, but that also allow binding of the phage to the target molecule and/or target microorganism, if present. The binder may then be washed under conditions sufficient to remove a substantial portion or all of any phage not bound to a target molecule and/or target microorganism without interrupting binding between the binder and target molecule and/or target microorganism and target molecule and/or target microorganism and phage. Then, the phage may be released by washing the binder under conditions that allow release of the phage from the target molecule and/or target microorganism. Conditions may be selected such that, after release, the phage remains able to infect a bacterium with reporter genetic material. The released phage may be used to infect a bacterium or bacteria with the reporter genetic material. The presence of this reporter generic material may then be detected. For example, the reporter genetic material may confer luminescence upon the infected bacteria, which may then be detected. Reporter genetic material may also be further amplified after infection, for example by expansion of the phage in the infected bacteria followed by further infection of nearby bacteria.

The number of eluted phage, in some embodiments, may be the same or substantially the same as the number of phage to which a target molecule and/or target microorganism was bound (e.g., the number of binder-target molecule/target microorganism-phage complexes applied to or on a column). One or more target molecules and/or target microorganisms may bind to a single phage particle (e.g., where the surface of a phage includes more than one surface molecule and/or where each surface molecule binds two or more target molecules and/or target microorganisms.

In a specific embodiment, M13 filamentous phage may be genetically engineered to create a reporter phage that also displays a specific binding peptide on its surface. The reporter phage may, for example, include genetic material able to cause infected bacteria to become luminescent. The genetically engineered phage may serve as a bioamplifiable tag that specifically binds the target molecule and/or target microorganism and amplifies the reporter signal (e.g. light) upon infection of *E. coli*. The infected *E. coli* may produce light and also amplify the signal by releasing 500-1000 new progeny phages which may infect other *E. coli* cells and produce more light.

Staphylococcal enterotoxin B (SEB), along with botulinum, ricin and ϵ-toxin may be among the most likely agents to be used as an aerosolized biological warfare agent against U.S. forces (Greenfield R A et al., (2002) *Am J Med Sci* 323, 326-340). SEB is one of five closely related enterotoxins (SEA, SEC, SED and SEE) produced and excreted by the human pathogen *Staphylococcus aureus* during growth. Although SEB may be inherently less toxic than, for example, botulinum toxin, patients exposed to SEB become seriously ill experiencing fever, shortness of breath, chest pain, vomiting and diarrhea. These conditions may incapacitate a fighting force for up to about two weeks. Higher toxin exposure may lead to septic shock and death. As a threat agent, SEB may be used primarily as an aerosol hazard; however, SEB may be a common causative agent of food poisoning upon digestion of improperly handled food. Therefore, SEB potentially may be delivered via inhalation, such as through aerosols, or ingestion, such as through deliberately contaminated water or food supplies. Both portals of toxin entry are toxic to humans and there is currently no human vaccine against SEB poisoning.

One specific example embodiment of the disclosure invention relates to the detection system of FIG. 1. In this example, the target molecule may include staphylococcal enterotoxin B (SEB) and the phage may contain reporter genes which may be the luxAB genes from *Vibrio harveyi* (e.g., Accession No. E12410, version 1, last updated Apr. 20, 2006). These genes may confer luminescent properties upon bacteria. The filamentous M13 phage may be used as a detector and bioamplifiable reporter for the detection of SEB. The M13 phage may be genetically engineered to contain the *Vibrio harveyi* luxAB genes to create a genetically engineered phage capable of causing infected bacteria to produce light. In addition, the genetically engineered phage may be modified to display a specific toxin binding peptide on its exterior surface or coat. Specifically, the peptide may bind SEB.

SEB contaminated samples or samples suspected of containing SEB may be liquefied, if needed, and passed through a column containing immobilized SEB specific antibodies. Only SEB may specifically bind to the antibodies while nonspecific particles may pass through the column. The genetically engineered phage may then be passed through the column where it may specifically bind to any SEB present. Unbound phage may be washed away. The SEB-binding phage may be eluted from the column into a solution containing M13 phage competent *E. coli* cells. Phage infection of *E. coli* may result in phage DNA replication, luxAB reporter gene expression, light emission, the production of approximately 1000 new virions on the first infection cycle, or any combinations of the above. Newly produced virions may be extruded from the cell without cell lysis and may infect other *E. coli* cells, resulting in exponential amplification of the signal until a certain amount of time has passed or the number of *E. coli* hosts are exhausted.

Light emission may occur without processing of the sample and may be sensitively detected through multiple commercially available means without the use of expensive equipment or specific expertise. The amount of light produced and the time taken to generate the signal may be directly proportional to the amount of toxin present in the original sample. If no SEB is present in the sample, then no light may be detected. Alternatively, if the amount of SEB in the sample is below a certain threshold, then no light may be detected, particularly within a specific time frame.

In some embodiments, a binder may include an SEB binding peptide. For example, an SEB peptide may be isolated from a phage display library and exhibit strong binding to SEB (e.g., Goldman ER (2000) *J Mol Recognit* 13, 382-387). Specificity experiments using other staphylococcal enterotoxins (SEA, SEC and SED) with the peptide of Goldman, for example, showed no cross reactivity with SEA and SED but significant cross-reactivity with SEC, which shares approximately 65% sequence identity with SEB. Therefore, this capture phage may also detect SEC in addition to SEB. The DNA sequence encoding the SEB peptide (WHKAPRAPAPLL; SEQ ID NO. 1) may be cloned into the M13KE phage display vector (New England Biolabs, Inc., Beverly, Mass.) so that it will be fused in frame with the pIII coat protein sequence. The resulting phage may display five copies of the fusion peptide coat protein on the surface of each virion. Error prone PCR and phage display studies may be performed using the conserved SEB codons and randomizing the flanking residues in order to optimize the affinity and specificity of the peptide. The phage may also be genetically engineered to contain the *V. harveyi* luxAB reporter genes under the control of optimized *E. coli* transcriptional and translational expression signals to maximize reporter gene expression and light emission (Schofield D A et al., (2003) *Appl Environ Microbiol* 69, 3385-3392). The filamentous M13 phage may be an appropriate phage for this embodiment because: (i) Reporter genes such as luxAB may be inserted into the intergenic region of the M13 phage genome without any loss of phage function; (ii) M13 infects *E. coli* within 2 minutes and releases progeny phage after 20 minutes, thus offering a fast signal response time; (iii) M13 phage, in comparison to lytic bacteriophage, do not lyse their host, but instead extrude progeny virions through the bacterial membrane. Consequently, infected *E. coli* hosts may continually produce light as well as amplify the signal by producing new progeny phage; (iv) M13 phage display vectors enabling cloning and in frame fusion with the phages coat protein are commercially available and (v) Amplification of the number of copies of the luxAB genes may occur immediately after phage infection because the single stranded phage DNA encoding the luxAB genes may be converted into multiple double stranded replicative forms.

A binder may include or be linked to, according to some embodiments a gel, bead, column, well, and/or other matrix. In some embodiments, a binder may be configured and arranged to permit rapid and/or automated separation of phage particles. For example, one or more columns may be configured to permit spinning along their longitudinal axis.

In another embodiment, phagemid vectors may be used instead of phage to encode the displayed molecule and the reporter genetic material. The phagemid vectors (which may contain a phage and plasmid origin of replication) may be grown as plasmids containing the genetic information for the reporter gene and displayed surface molecule and may be packaged into recombinant M13 phage with the aid of a helper phage such as M13KO7 or VCSM13. The recombinant phage may be used as described herein to infect bacteria and produce a signal if the target molecule and/or target microorganism was present. However, the recombinant phage may not be able to reinfect other bacteria and produce progeny phage. Under these conditions, helper phage such as M13KO7 and VCSM13 may be added to the infected bacteria in order to produce recombinant progeny phage and further amplify the signal.

In another embodiment, lytic phage may be used instead of filamentous phage to display the capture molecule on its surface. Alternatively, phage infection may be detected by the release of phage encoded proteins/recombinant proteins into the medium. The presence of the target molecule and/or target microorganism may be detected upon lytic phage infection of the target bacteria as indicated by rapid clearing (lysis) of the infected bacteria. Alternatively, phage infection may be detected by the release of bacterial components into the surrounding media. For example, bacterial lysis may be detected by an increase in the concentration of ATP in the medium released from the bacterial cell upon cell lysis.

luxAB may be selected as a reporter because expression in *E. coli* may be sensitively detected and/or because detection may require little to no processing of the bacteria. Detection may require addition of a substrate, such as the aldehyde substrate decanal, which may be readily capable of passing through the bacterial membrane and entering the cell. In addition, light detector instruments are readily available and may be used in this embodiment. A temperature controlled portable light sensor may also be used.

In another embodiment, a bacterium may include a reporter nucleic acid. A reporter nucleic acid in the bacteria may be operably linked to an expression control sequence (e.g., a promoter). An expression control sequence may be selected or configured to be active only in the presence of an activator protein, which the bacteria do not possess. A phage may be selected or configured to include an activator protein that is strictly required for expression of a reporter nucleic acid. In this embodiment, phage infection of bacteria may supply the activator protein, resulting in reporter gene expression which may be indicative of the target molecule and/or target microorganism being present.

In another embodiment, an expression control sequence operably linked to a reporter nucleic acid may include a repressible promoter (e.g., including repressor protein binding sites). The phage may be selected or configured (e.g., genetically modified) to include multiple sequences of a repressor protein binding site. In the absence of phage infection, the bacterial promoter may be inactive (repressed) such that there is no expression of the reporter nucleic acid. Upon phage infection, the phage DNA containing the multiple repressor binding site is present and amplified, which titrates the bacterial repressor protein leading to promoter activation and expression of the reporter nucleic acid.

In another embodiment, neither the phage or the bacteria may contain the reporter genetic material. Instead, the target signal may be detected after phage infection by the increase in progeny phage released by the bacteria. This may be achieved using anti M13 antibodies and a generic immunoassay/or a quantitative PCR assay using the phage DNA as template.

Both specific and nonspecific SEB column binding may be used. Use of specific binders may reduce the chance of false positives. Commercially available SEB specific antibodies or nonspecific resins may be used in combination with deliberately spiked SEB water samples. For example, fused silica capillaries coated with SEB antibody may effectively capture SEB (Koch S et al., (2000) *Biosens Bioelectron* 14, 779-784). The different immobilization options may bind to the different isoforms of the SEB toxin. Conditions sufficient or optimized for efficient phage-SEB binding, the removal of non-binding phage and the elution of phage specifically binding SEB may be provided.

Non-specific binding of the phage to the column and incomplete removal of non-specifically bound phage may result in false positives. Different column supports may be used to minimize non-specific phage binding. For example nitrocellulose membranes and impermeable glass or plastic beads and magnetic beads may be used. Solid supports may be housed in other constructs besides columns such as centrifugal devices, microplates, and capillary tubes to improve the efficiency of the assay. Because filamentous phage are resistant to extreme conditions, high stringency washes and elution solutions may be used. The wash may and elution solution may be selected to maximize phage elution without compromising phage infectivity or with acceptable compromise of phage infectivity. For example, phage are resistant to acidic buffers of pH 2.2, alkaline buffers such as 0.1 M triethylamine and urea concentrations up to 6 M. In addition, specific elution of the phage without releasing phage that may be bound non-specifically to the column may be achieved through competitive elution using excess purified peptide or other molecule which may compete with phage-SEB binding.

M13 phage specifically infects *E. coli* cells containing the F conjugative plasmid. The optimal conditions for generating phage susceptible $F^+$ *E. coli* cells may be the mid stages of exponential growth. Active metabolism also may be desirable or required for luxAB expression and light emission. How quickly the reporter M13 phage will produce a detectable light signal upon infection may vary. However, the expression of M13 genes may be detected 2 minutes after phage infection and the release of phage progeny occurs 15-20 minutes later. In addition, *listeria* phage containing the luxAB reporter genes may produce a detectable signal 15-20 min after infection of *listeria* cells. Therefore, in certain embodiments, the time required to produce a signal after *E. coli* infection may be measured in minutes rather than hours. The amount of toxin present in the sample may be correlated to the amount and speed of signal produced.

In other embodiments, the *E. coli* may be genetically engineered to be rendered more susceptible to phage infection leading to faster response times. This may be achieved for example, by genetically engineering the *E. coli* to express more receptors (F pili) for the M13 phage (Malmborg et al., 1997. J. Mol. Biol. 273: 544-551). For example, *E. coli* only express up to 3 pili/bacterium under ideal conditions. Genetically modified bacteria that express more pili/bacterium may be more susceptible to phage infection. Since bacteria differentially express F pili at different stages of growth, continuous expression of F pili from a continuously expressed promoter in genetically engineered bacteria may also render them more infectable than wild type bacteria and may thus be more suitable for use in a kit. In addition, the sequence of the F pili may be deliberately mutated by error prone PCR for example, in order to obtain pili that are more resistant to environmental extremes. This may be useful for kit testing in a non laboratory environment.

In other embodiments, a peptide, antibody, nucleic acid, or fragments thereof that bind to any target of interest (e.g., toxin) may be placed on the phage coat. A detection system and method may be used for identification and detection of any biological molecule or entity, such as a virus, bacteria, protein, biomarker, or bioregulator. For example, peptides may be genetically engineered to specifically bind to inorganic compounds and may be used for the identification and detection of metals, oxides and other technological compounds.

Because phage display may screen billions of different peptides and identify high affinity peptide binders to the target of choice, phage display may be used to adapt the detection system and method to detect any toxin or biomarker of disease. Changes may also be made by changing the binder and column capture characteristics.

Peptides may also be designed to bind to multiple targets, particularly if the targets are similar, or the phage may be engineered to express more than one type of peptide. Alternatively, recombinant phages displaying unique peptides may be pooled to contain a mixed phage population, each potentially binding a different target molecule and/or target microorganism; the mixed recombinant phage each displaying unique peptides may also contain different reporter genes that produce different signals depending on the target molecule and/or target microorganism. This may allow simultaneous detection of more than one target molecule and/or target microorganism. Such detection may be particularly useful where the benefit of knowing quickly and with one test that any of a number of targets are present outweighs any determination of the specific target identity and/or amount.

The genetically engineered phage may be modified by changing the specificity of the displayed peptide on the phage coat using phage display methods. Additionally, the phage may be engineered to contain other reporter genetic material such as a fluorescent protein, including green fluorescent proteins, and the phage may be further engineered to enhance its utility as a detection tool. For example, the phage may be engineered to express a higher number of binding peptides on its coat.

The detection system and method may also be used in concert with automated aerosol collection techniques (e.g., Hindson B J et al., (2005) Anal Chem. 77, 284-289) for the detection of aerosolized SEB or other target molecules and/or target microorganisms.

In a particular embodiment, a detection system and method may be used to detect bioregulatory molecules. Such detection may be important because these molecules may have the potential to function at very low doses and thus may be more difficult to detect in a useful manner.

In another embodiment, the detection system and method may be adapted to detect *staphylococcus*. Staphylococcal enterotoxin food poisoning may be one of the most common forms of food borne illness following the ingestion of contaminated food such as dairy products.

A system may include a column having an inner and outer surface, wherein the inner surface is at least partially coated with a binder molecule. A column may be in liquid communication with a loading chamber configured to apply solutions (e.g., test sample, wash solutions) to the column. A column may be in liquid communication with a collection chamber configured to receive liquid passed or forced through the column. A collection chamber may be configured to receive liquid from the column in one or more fractions.

In some embodiments, a bioluminescent phage detection system may be used to diagnose anthrax. The phage may be used to identify the presence of *B. anthracis* in clinical samples taken from patients suspected from suffering from the anthrax disease. The phage may also be used to diagnose anthrax in livestock.

In some embodiments, a phage may be modified by integrating bactericidal genes into the Wβ lysogenic locus. Disrupting genes controlling lysogeny may create a lytic Wβ variant that may kill *B. anthracis*. Moreover, the addition of the bactericidal genes may increase the ability of the phage to kill *B. anthracis* under conditions not conducive to phage replication and lysis, such as low bacterial concentrations (threshold potential) and/or low bacterial metabolic activity. Bactericidal genes that may be expressed independent of lytic growth, may also kill host bacteria that otherwise may be resistant to lysis. Some examples of bactericidal and/or antibacterial encoding genes include doc, relA, mazF, PemK, genes that encode lytic enzymes, genes that encode molecules involved in programmed cell death, genes that inhibit transcription and/or translation, genes that encode membrane pores, genes that encode cell wall synthesis inhibitors, and combinations thereof.

EXAMPLES

Some specific embodiments of the disclosure may be understood, by referring, at least in part, to the following examples. These examples are not intended to represent all aspects of the disclosure in its entirety. Variations will be apparent to one skilled in the art.

Example 1

Construction of the Recombinant luxABM13 Phage

Figure 2:
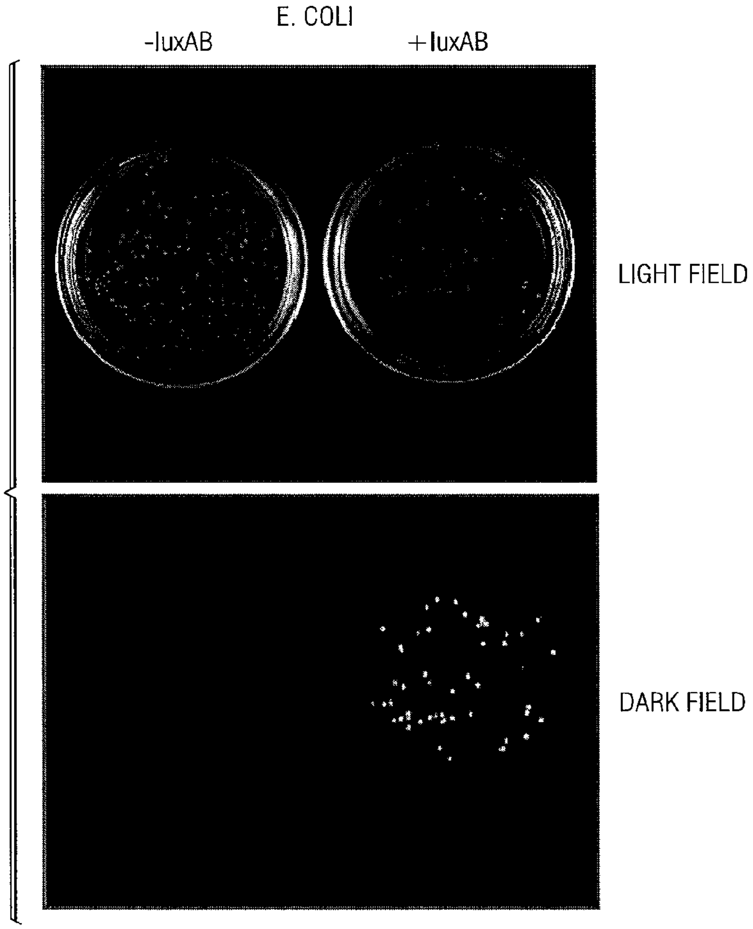
FIG. 2 illustrates an embodiment of the disclosure in which the functionality of the plasmid luxAB cassette was assessed by examining *Escherichia coli* (*E. coli*) cells under dark field illumination to view luminescent colonies.
Figure 3:
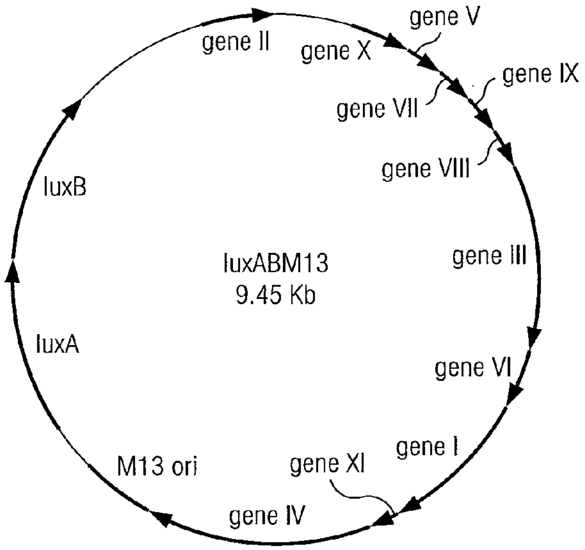
FIG. 3 illustrates a schematic map of a LuxABM13 plasmid in accordance with an embodiment of the disclosure.

The *Vibrio harveyi* 'light' genes, luxA and luxB were PCR-amplified using pQF110 (ATCC77113) as template. The PCR primers were designed to contain XbaI/BamHI and HindIII/XhoI, respectively, for directional cloning into the corresponding sites of pBluescript-pSK−. The 5' primers were also designed to contain a consensus *E. coli* ribosome binding site (TAAGGAGGTAAAAAA(ATG); SEQ ID NO. 2) (Schofield D A et al., (2002) *FEMS Microbiol Lett* 215, 237-42. An *E. coli* promoter containing consensus transcriptional signals (Schofield D A et al., (2003) *Appl Environ Microbiol* 69, 3385-3392) was cloned upstream (SacI/NotI sites) of luxAB and the transcriptional terminator TL17 (Wright et al. (1992) *EMBO J.* 11, 1957-64) was cloned downstream (Kpn I sites) of the luxA and luxB genes. To test whether the luxAB expression vector was functional, the luxAB plasmid was transformed into *E. coli* ER2738 and the resulting colonies were examined under dark field illumination in the presence of the substrate decanal. In the absence of luxAB, luminescent colonies were not obtained (FIG. 2); however, when luxAB was present, luminescent colonies were clearly visible. This demonstrated that the optimized luxAB cassette was functioning in *E. coli*. The luxAB expression cassette, which was flanked by Sph I sites, was then cloned into the same sites of bacteriophage vector M13KE (New England Biolabs) to create luxABM13 (FIG. 3).

Example 2

Analysis of the Efficiency of the Recombinant Phage

Cloning of the luxAB cassette into M13KE increased the genome size from approximately 7.2 kb to 9.4 kb. Although, fairly large fragments may be cloned into M13 without any loss of phage function, the size of DNA fragment, the orientation, and the sequence may negatively impact the 'fitness' of the phage. To check the 'fitness' of the recombinant phage, the burst size and the latency of the recombinant luxABM13 phage was compared to the wild-type M13 phage.

Example 3

Burst Size

The burst size may be the number of progeny phage released after the initial infection. *E. coli* ER2738 cultures ($OD_{600}$ of 0.605, $5.8\times10^8$ CFU/mL) were infected with wild-type or recombinant phage at time 0 with a multiplicity of infection (MOI) of approximately 10. After 40 min, the culture supernatants were passed through a 0.2 μm filter and enumerated for phage using the soft agar overlay technique (Westwater et al. (2003) Antimicrob Agents Chemother 47, 1301-7).

The results indicated that the recombinant luxABM13 had a slightly lower burst size than the wild-type M13 phage (Table 1).

TABLE 1

Burst size of the wild-type M13 phage and recombinant luxABM13 phage.

| Time (min) | PFU/mL *(SD) M13 | PFU/mL *(SD) luxABM13 |
|---|---|---|
| 0 | $7.5 \times 10^9$ ($7.5 \times 10^7$) | $7.6 \times 10^9$($8.7 \times 10^7$) |
| 40 | $1.6 \times 10^{11}$($2.0 \times 10^9$) | $5.9 \times 10^{19}$($1.5 \times 10^9$) |

*Average of triplicate infections followed by the standard deviation in parentheses.

Example 4

Latency

Figure 4:
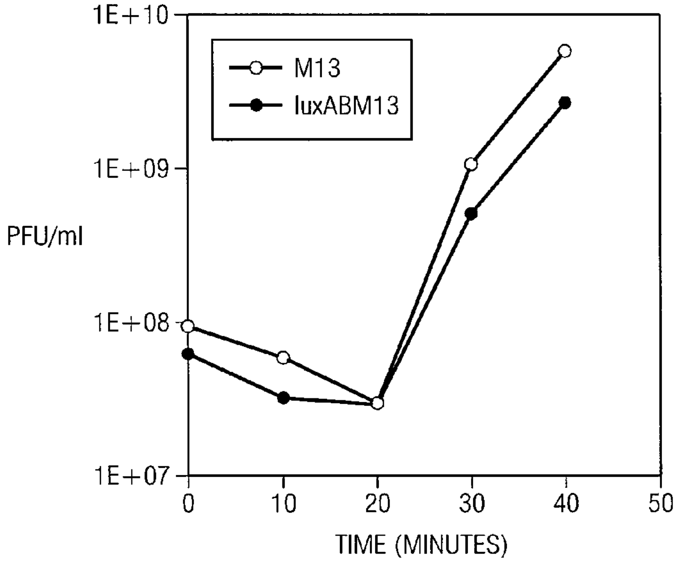
FIG. 4 illustrates a comparison of the latency period between a luxABM13 and wild-type M13 in accordance with an embodiment of the disclosure.

Latency may be the time from infection until the first new, progeny phage are released from the host cells. *E. coli* ER2738 cultures ($OD_{600}$ 0.645, $7.5\times10^8$ CFU/ml) were infected at time 0 with an MOI of 0.124 and 0.084 for the wild-type and luxABM13 phages, respectively, and phage progeny release was monitored using the soft agar overlay technique. The results indicated that the latency period of luxABM13 was very similar to the wild-type M13 phage and occurred about 20 min after infection (FIG. 4).

Example 5

Optimal Stages of *E. coli* Growth for luxABM13 Infection

Figure 5:
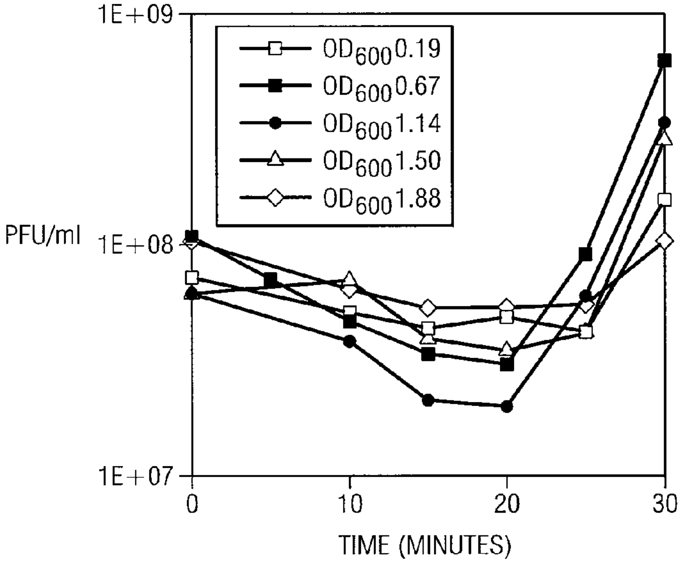
FIG. 5 illustrates phage infection during various stages of *E. coli* growth in accordance with an embodiment of the disclosure.

M13 phage specifically infects *E. coli* cells containing the F conjugative plasmid. The optimal conditions for generating phage susceptible r *E. coli* cells may be the mid stages of exponential growth. To verify that the mid stages of exponential growth were optimal for luxABM13 infection, *E. coli* ER2738 was harvested at various stages of growth, normalized to an $OD_{600}$ of approximately 0.7, and infected with luxABM13 (MOI of approx. 0.1). In agreement with the published literature for wild-type M13 phage, the mid stages ($OD_{600}$ 0.67-1.14) of *E. coli* exponential growth was also found to result in the shortest latency period for luxABM13 (FIG. 5).

Example 6

Optimal *E. coli* Concentrations for Phage Infection

Figure 6:
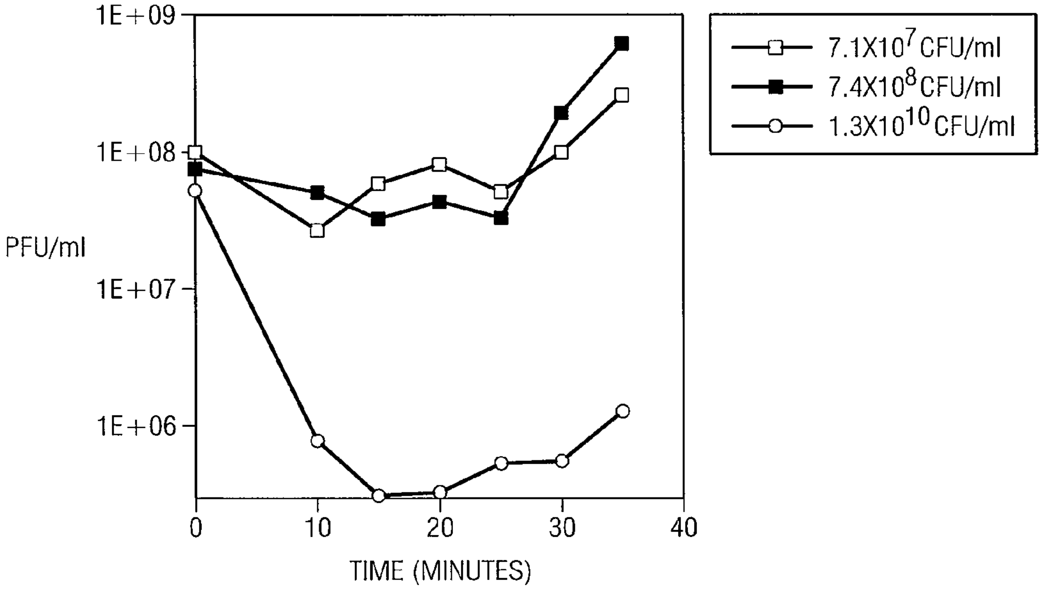
FIG. 6 illustrates luxABM13 infection at various *E. coli* densities in accordance with an embodiment of the disclosure.

The density of the *E. coli* culture may be an important parameter affecting the speed with which a phage finds and infects a host. To determine a desirable concentration(s) for the phage/*E. coli* interaction, *E. coli* ER2738 was grown to an $OD_{600}$ of 0.65. The culture was harvested by centrifugation, and resuspended in prewarmed media to 0.1 of the original volume. The culture was then diluted as appropriate to generate a 10, 1, and 0.1 concentration of the original culture. Cultures (100 μl) were infected with $1\times10^7$ luxABM13. The results indicated that a high density of *E. coli* ($1\times10^{10}$ CFU/ml), resulted in a quick decrease in the number of 'available' phage in the culture supernatant. This suggests that the high density was preferential for the phage/host interaction (FIG. 6).

Example 7

Time to Light Signal

Figure 7:
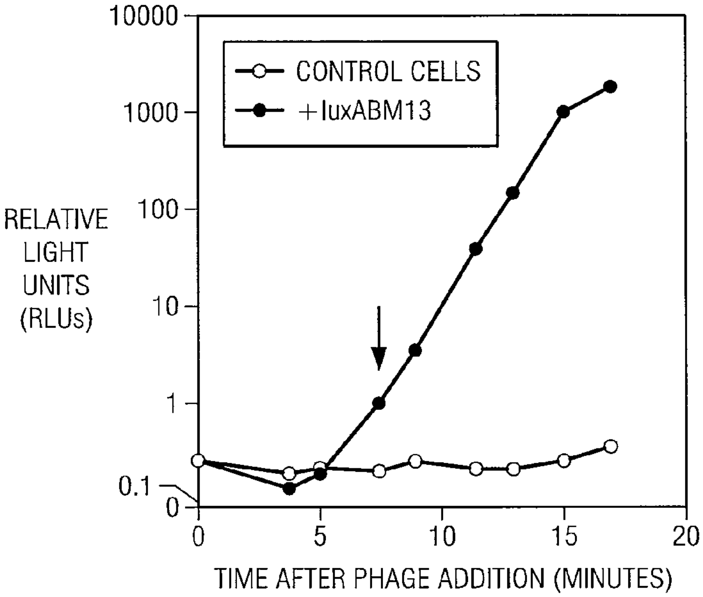
FIG. 7 illustrates signal response time from phage addition to detectable light above background in accordance with an embodiment of the disclosure.

M13 gene expression may be detected 2 minutes after phage infection while the release of phage progeny may occur 20 minutes later. *listeria* phage containing the luxAB reporter genes may produce a detectable light signal 15-20 min after infection of *listeria* cells. To investigate how quickly the luxABM13 phage may infect *E. coli* and produce a light signal, *E. coli* ER2738 cells were harvested at $OD_{600}$ 0.6, concentrated 10-fold ($7.1\times10^9$ CFU/ml), and infected with luxABM13 at an MOI of approximately 8. Cultures were harvested at the designated times after infection and monitored for light production using the luminometer LMII[384]. The data indicated that the signal response time (time period from phage infection to detectable light production above uninfected *E. coli*) was 7.5 min (FIG. 7).

Example 8

Relationship Between Amount of Input Phage and Light Output

Figure 8A:
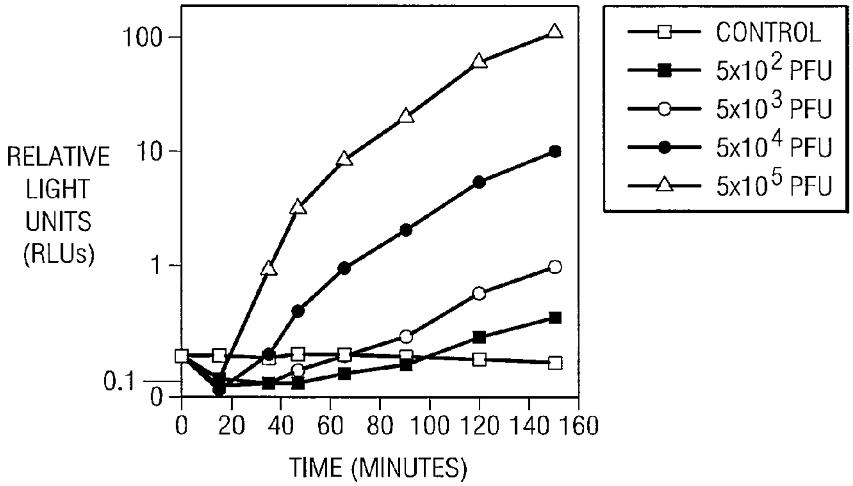
FIG. 8A illustrates a dose response curve with from $5\times10^2$ to $10^5$ phage in accordance with an embodiment of the disclosure.
Figure 8B:
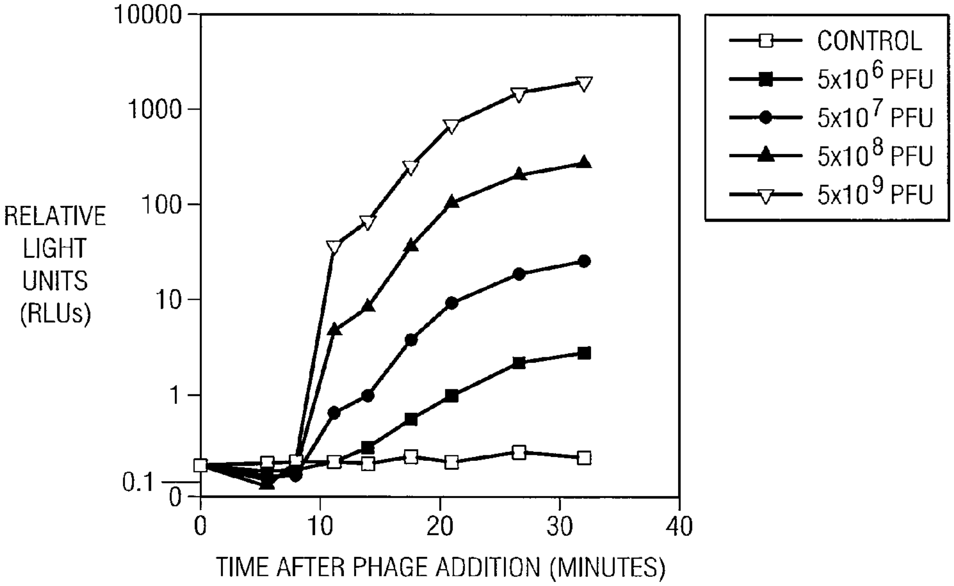
FIG. 8B illustrates a dose response curve with from $5\times10^6$ to $10^9$ phage in accordance with an embodiment of the disclosure.

It may be important to be able to detect and also quantify (relatively) the target in the original sample. To investigate if the amount of light produced correlates with the amount of input phage, 10-fold serial dilutions were performed on the stock phage ($10^9$-$10^2$ plaque forming units, (pfu/mL)) which was then used to infect *E. coli* ER2738 ($OD_{600}$ 0.6-0.7). As the amount of input phage decreased, the amount of light produced decreased (FIGS. 8A and 8B). In addition, as the amount of input phage decreased, the signal response time increased. This indicates that it should be possible to quantify (relatively) the amount of target in the original sample by the amount of light produced and the time taken to produce a light signal.

Example 9

Sensitivity

Figure 9:
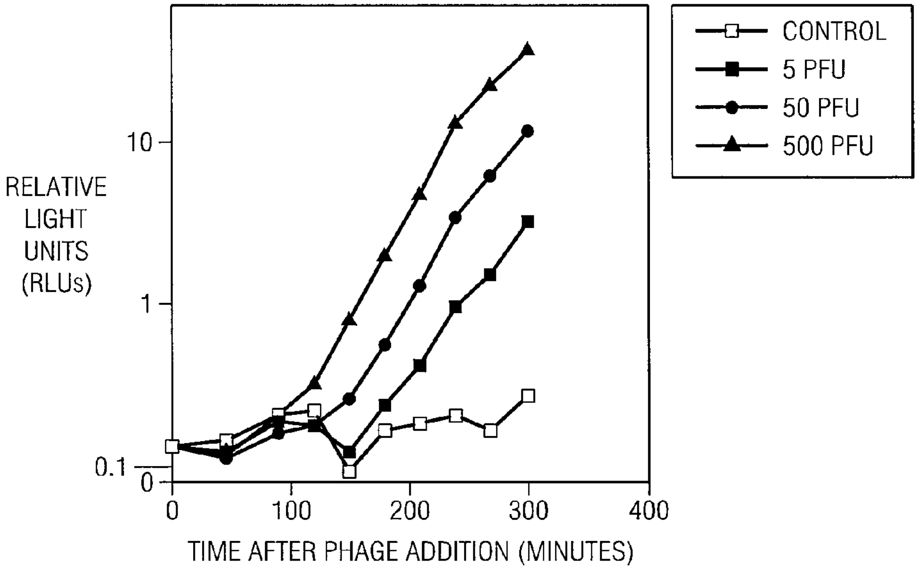
FIG. 9 illustrates assay sensitivity in accordance with an embodiment of the disclosure.

According to some embodiments, it may be desirable, important, and/or vital for the assay to be sensitive since the target may be present at very low concentrations. To determine the sensitivity limits of the assay, *E. coli* ER2738 ($OD_{600}$ of 0.35) were infected with 5, 50, and 500 luxABM13 pfu and monitored for light production over time (up to 300 min). As the number of input phage dropped from 500 to 5 pfu, the signal response time increased and the amount of light decreased (FIG. 9). Nevertheless, as few as 5 pfu may be detected, albeit after a longer signal response time (200 min). This indicates that the methodology has the potential (assuming efficient column binding and recovery) to detect single copies of the target molecule and in that respect, has sensitivity characteristics that are comparable to PCR.

Example 10

Effects of Freezing and Storage on Infectibility and Latency

Figure 10:
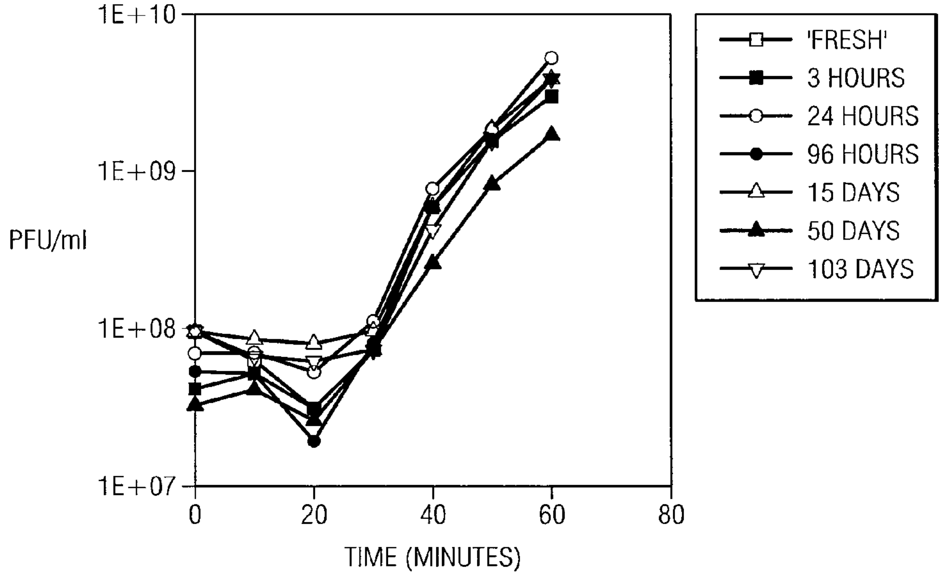
FIG. 10 illustrates LuxABM13 latency using cells stored under various conditions in accordance with an embodiment of the disclosure.

Phage may be resistant to environmental extremes and, in some embodiments, may be stored for months or years without a significant loss in phage infectivity. If phage susceptibility is lost after long-term storage, it may return although it is not clear in every case how long this may take. This may be an important consideration if the detection device is to be used outside of the laboratory and exhibit a quick response time. Therefore, experiments were performed that examined luxABM13 latency (time from infection to new phage progeny produced) using *E. coli* cells that have been stored frozen for varying lengths of time at −70° C. *E. coli* ER2738 were grown overnight in Luria Bertani (LB) broth containing tetracycline (25 μg/ml), diluted 1:100 (0.5 into 50 mL) and grown at 37° C. at 235 rpm. After 3-4 hours, cultures ($OD_{600}$ 0.650, 45 ml) were chilled on ice, harvested by centrifugation, resuspended in cold 1.5 ml 10% glycerol and flash frozen (100 μl aliquots) in dry ice/ethanol. Cells were stored at −70° C. until the time of experiment. At the designated storage times, cells (300 μl) were defrosted on ice, and mixed with prewarmed LB (9.7 mL). Cells were immediately measured (colony counting after overnight growth) for CFU (approx. $6\times10^8$ CFU/ml) and infected with the luxABM13 phage at an MOI of approximately 0.1. At the designated times, culture supernatants (ice, 2 min bench top centrifuge, 0.2 μm filter) were enumerated for phage using the plaque assay (FIG. 10). LuxABM13 latency was compared using 'fresh' cells and cells which had been stored at −70° C. for up to 103 days. The results indicated that the luxABM13 latency period was very similar using either fresh or stored *E. coli* cells, irrespective of the length of storage time. Therefore, freezing and storage of *E. coli* ER2738 under the conditions tested does not significantly affect the time it takes for luxABM13 to infect and produce progeny phage.

Example 11

Light Production and Signal Response Time Using Stored *E. coli* Cells

Figure 11:
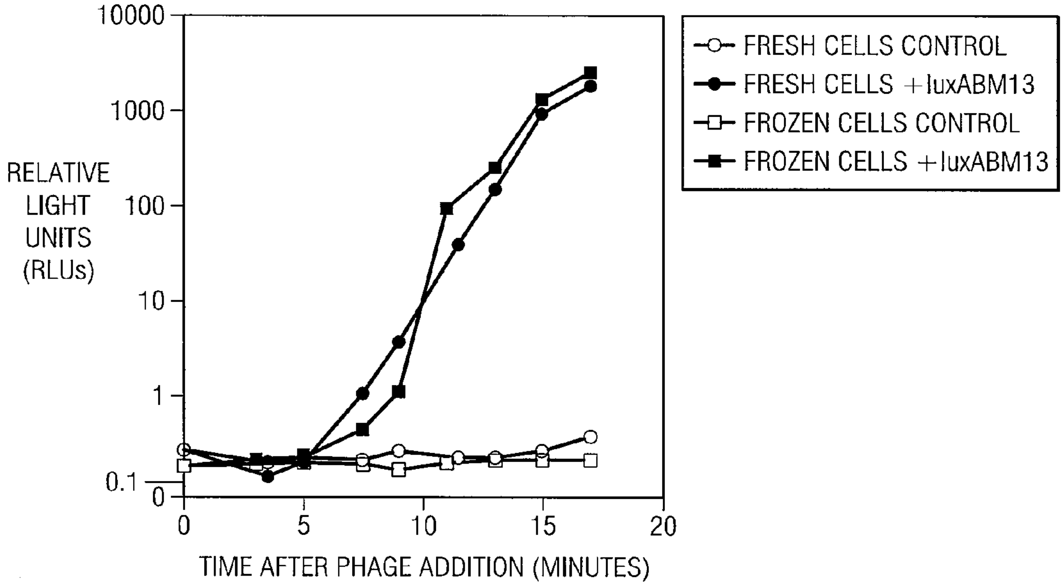
FIG. 11 illustrates light production and signal response times using cells stored under various conditions in accordance with an embodiment of the disclosure.

Active metabolism may be required for luxAB expression and light emission. Although the luxABM13 latency may be similar irrespective of whether fresh or frozen *E. coli* cells are used, it was of interest to examine if stored (frozen) cells negatively affected the ability of luxABM13 to produce light. Therefore, the signal response time of fresh and stored cells, infected with the luxABM13 phage, was examined. Freshly prepared ($OD_{600}$ of 0.6) or stored (frozen at −70° C. for 90 days) phage competent *E. coli* ER2738 cells, were infected with a MOI of 8 and 16, respectively and monitored for light production. The amount of light produced and the signal response time was similar irrespective of whether fresh or stored cells were used (FIG. 11). This indicates that prior storage at −70° C. for 90 days does not negatively affect the ability of *E. coli* ER2738 to be infected with luxABM13 and produce light.

Example 12

Temperature Sensitivity of *E. coli* Produced luxAB Proteins

Figure 12:
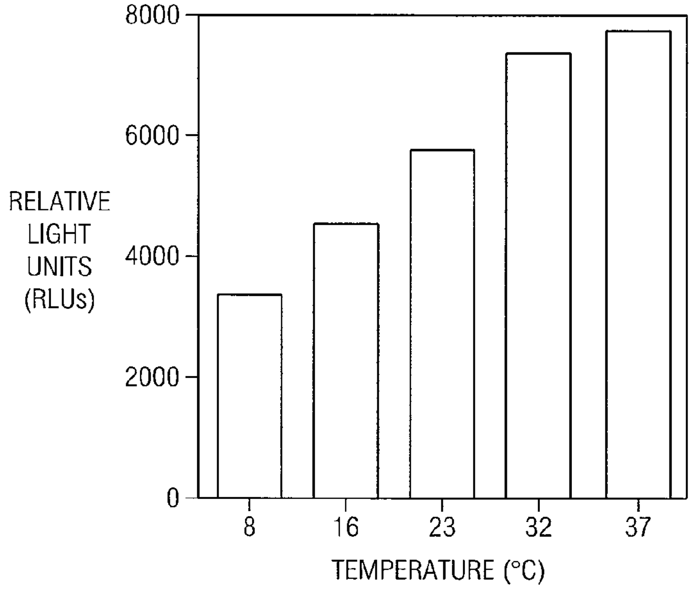
FIG. 12 illustrates luciferase activity at various temperatures in accordance with an embodiment of the disclosure.

In *Listeria monocytogenes* LuxAB protein synthesis and stability may be temperature sensitive. Maximum light production occurred at 20° C., while incubations at higher temperatures (30 and 37° C.) significantly reduced luminescence. To investigate whether light production was temperature sensitive in *E. coli, E. coli* ER2738 harboring a pBLUESCRIPT plasmid containing the luxAB cassette, was grown until mid log phase at 32° C. Equal cell aliquots were then incubated at the designated temperatures for 10 min prior to assaying for luciferase (light) production. The results indicated that light production in *E. coli* was temperature dependent (FIG. 12); however, in contrast to *Listeria*, maximum light production was observed at elevated (37° C.) temperatures, and activity decreased as the temperature decreased. These results are for a short (10 min) incubation at the designated temperatures, and are independent of infection, but are dependent on *E. coli* growth, and gene/protein expression. Repeat experiments should be performed examining the activity of enzyme lysates at the different temperatures.

While embodiments of this disclosure have been depicted, described, and defined by reference to specific example embodiments of the disclosure, such references do not imply a limitation on the disclosure, and no such limitation is to be inferred. The subject matter disclosed may be capable of considerable modification, alteration, and equivalents in form and function, as will occur to those ordinarily skilled in the pertinent art and having the benefit of this disclosure. For example, a variety of phage and bacteria pairs may be used. Other viruses and non-bacterial cells (e.g., yeast) may even be used in some embodiments. Similarly, a number of different types of reporter genetic material and detection systems may be used. The depicted and described embodiments of this disclosure are examples only, and are not exhaustive of the scope of the disclosure.

Prophetic Example 13

Some embodiments of this disclosure may relate to the threat of bioterrorism in relation to food safety. *Bacillus anthracis*, the causative agent of anthrax, is a Category A pathogen that may be used in a bioterrorist attack. The primary area of concern is the deliberate contamination of 'ready to eat' or minimally processed foods. Some embodiments of this disclosure may provide the foundation for a methodology that can specifically detect anthrax contamination of food.

The 'natural' incidence of anthrax is extremely rare in the U.S.; however, the ease with which hostile countries and terrorist organizations may obtain biowarfare agents, such as *B. anthracis*, has highlighted the need for detection, surveillance and decontamination methodologies. The Center for Disease Control (CDC) has listed *B. anthracis* as a Category A bacterial pathogen most likely to be used in a bioterrorist attack. Exposure may occur by any of three major routes: inhalation, cutaneous or gastrointestinal (GI). In particular, GI anthrax, which occurs through the ingestion of contaminated foods, is considered to be extremely dangerous because it is very difficult to diagnose. The disease presents nausea, vomiting and diarrhea as common symptoms and if appropriate antibiotics are not administered in a timely manner, patient prognosis is very poor with mortality rates exceeding 40%. The primary area of concern may be deliberate contamination of 'ready to eat' or minimally processed foods, which do not receive the protective benefit of cooking. Although sanitizers are used to wash fresh produce, *Bacillus* spores may be extremely resistant to chemical and physical insult and these treatments may have limited effectiveness. Therefore, methodologies are urgently required for detecting *B. anthracis* on contaminated food (e.g., deliberately contaminated food).

Some embodiments of this disclosure may provide a light-tagged (e.g., luxAB) phage that can specifically detect and kill *B. anthracis*. For example, some embodiments of the disclosure may generate a phage detection system that may: (i) bioluminesce if *B. anthracis* is present; (ii) detect viable (potentially infectious) cells only; (iii) require only minimal exogenous substrates or consumables; (iv) be environmentally friendly and/or easy to produce in bulk quantities; (v) be portable; (vi) be visually assessed using a simple hand held illumination device, and/or (vii) kill *B. anthracis* following detection. Some embodiments of this disclosure may enhance food safety and/or may be directly beneficial for the detection and decontamination of anthrax-contaminated buildings and offices.

Prophetic Example 14

Background and Rationale

In 1931, Cowles first described a *B. anthracis* phage that was active against all 11 *B. anthracis* strains tested but were also active against non-*B. anthracis Bacillus* species. A 'specific' lysogenic *B. anthracis* phage was later identified by McCloy in 1951, called phage W (subsequently renamed wβ). Wβ infected all 171 strains of *B. anthracis* analyzed, 2 of 54 *Bacillus cereus* strains (the 2 positive strains were classed as "atypical" strains more closely related to *B. anthracis* than *B. cereus*), but did not infect 10 other *Bacillus* species; however, the phage could not infect smooth (encapsulated) *B. anthracis* strains. In 1955, Brown and Cherry isolated a lytic variant of Wβ, designated γ. Both Wβ and γ were 'specific' to *B. anthracis*; however, γ was also able to lyse smooth *B. anthracis* strains. In a recent study, γ phage was able to infect and lyse 49 out of 51 *B. anthracis* strains collected from diverse geographical locations such as Pakistan, Canada, Argentina, England, U.S., and South Africa. Consequently, due to its species specificity and broad strain susceptibility, γ is routinely used as a standard rapid clinical diagnostic tool by the CDC and various public health laboratories for the identification of *B. anthracis.*

Wβ and γ are morphologically identical: they are similar to the siphoviridae family of tailed phages (double stranded (ds) DNA viruses) consisting of an icosahedral head and a long contractile tail. The Wβ and γ genomes were recently sequenced (40,864 bp and 37,373 bp, respectively) and were found to encode for 53 open readings frames each. Comparison of Wβ and γ indicated that the γ variant evolved from lysogenic Wβ by deletions and modification at the lysogenic locus and by key mutations in the tail fiber gene, wp14. The major genetic differences between Wβ and γ were: (i) a 25 bp deletion between wp25 and wp26 (in the lysogenic locus); (ii) a 2,003 bp deletion in wp28 and wp29, which encodes for a C1 repressor homolog (controls lysogenic functions), and (iii) 69 point mutations in the tail fiber gene wp14. These differences have been attributed to the lysogenic verses lytic lifestyle, and the ability to infect rough (non-encapsulated) strains only. A key difference between Wβ and γ, which is unrelated to lifestyle and host range, is that γ has also acquired a 1,360 bp antibiotic (fosfomycin) resistance module. The use of γ phage outside of the lab therefore, comes with the risk of the potential transfer of the γ antibiotic resistant module to infected *Bacillus* strains by phage-mediated gene flow.

Bioterrorist pathogen *B. anthracis* is not a common contaminant on foods, but the deliberate contamination of 'ready to eat' foods, or minimally processed foods is of vital concern because: (i) spores, which are infectious and in weaponized form, may be resistant to chemical and physical insult and are likely to be difficult to decontaminate using conventional food sanitizers; (ii) the 'ready to eat' contaminated food will not be cooked, and therefore, will not benefit from the protective benefit of heating, which can cause a significant reduction in spore viability; (iii) the daily consumption of fresh produce has increased 24% in the U.S. over the past 30 years, providing more opportunity for tampering, and (iv) GI anthrax is very difficult to diagnose and without appropriate antibiotics, results in high mortality (>40%). Consequently, detection methodologies that can quickly, easily, and specifically detect the presence of *B. anthracis* on deliberately contaminated foods are urgently needed.

Some embodiments of this disclosure may provide technology that will enhance food safety and potentially save lives. Some embodiments of this disclosure may relate to technology that is specific, cheap to produce, portable, quick, and/or discriminatory between viable (potentially infectious) and non-viable cells.

Prophetic Example 15

Some embodiments of this disclosure may provide methods for preparing a 'light producing' Wβ::luxAB phage that specifically detects *B. anthracis*. Results may demonstrate that Wβ::luxAB phage: (i) are viable, stable, and retain similar properties to the wild-type phage; (ii) can detect *B. anthracis* by emitting a bioluminescent signal; (iii) exhibit a fast signal response time; (iv) can be used to detect *B. anthracis* spores and vegetative cells, and (v) can detect viable cells only.

In addition, some embodiments of the disclosure may include modifying the Wβ tail fiber Wp14 protein to allow the phage to infect both rough and smooth (encapsulated) *B. anthracis* strains. In addition, some embodiments of the disclosure may integrate bactericidal genes into the Wβ lysogenic locus. Disrupting one or more genes controlling lysogeny may create a lytic Wβ variant that may kill *B. anthracis*. Moreover, the addition of the bactericidal genes potentially increases the ability of the phage to kill *B. anthracis* under conditions not conducive to phage replication and lysis, such as low bacterial concentrations (threshold potential) and low bacterial metabolic activity. Bactericidal genes that are expressed independent of lytic growth, may also kill host bacteria that were otherwise resistant to lysis. The disclosure, according to some embodiments, relates to generation of a phage that can specifically detect and kill *B. anthracis*. These embodiments have the potential to save lives, and to reduce the economic burden associated with health and business costs following an anthrax attack. A similar phage product (Intralytix) to be used for the eradication of *Listeria* cells on contaminated foods, has recently been approved by the FDA. In addition to food safety, some embodiments of the disclosure may provide a convenient means for monitoring the efficacy of chemical-mediated decontamination of anthrax-contaminated buildings and offices.

Prophetic Example 16

Production of *B. anthracis*-Specific Phage

The following processes relate to production of a *B. anthracis*-specific phage, genetically engineered with the luxAB genes, to detect *B. anthracis.*

Some embodiments relate to generating a *B. anthracis* luxAB reporter phage. LuxAB may be cloned into an expression cassette under the transcriptional and translational control of preferred *Bacillus* expression sequences. The expression cassette may be flanked by Wβ phage DNA. LuxAB may be integrated into a non-essential region of the Wβ genome by homologous recombination based on a double cross over event. Recombinant Wβ::luxAB may be identified and isolated based on the ability of infected cultures to emit light. luxAB integration may be verified by diagnostic agarose gel electrophoresis and PCR. The 'fitness' of the recombinant phage may be compared to the wild-type phage.

Some embodiments relate to feasibility studies to demonstrate that Wβ::luxAB may be used effectively as a *B. anthra-*

*cis* detection system. *B. anthracis* spores may be generated and Wβ::luxAB, in conjunction with spore germinating agents, may be analyzed for its ability to infect *B. anthracis* and produce a light signal. To demonstrate that the phage will detect viable cells only, bioluminescence assays may be performed using viable and heat-killed spores. The sensitivity limits of detection, the signal response time, and the dose-response characteristics in relation to the number of spores present may be determined. The thermal stability of LuxAB proteins in *B. anthracis* may be examined at different temperatures. Since the phage is expected to be used in a non-laboratory environment, Wβ::luxAB may be analyzed for its ability to remain infective at different pH's, at different temperatures, and over extended storage periods.

Prophetic Example 17

Generation of a *B. anthracis* luxAB Reporter Phage

*B. anthracis* detection methodologies may include microbiological techniques such as the γ phage lysis assay, lack of β-haemolytic activity, lack of motility, penicillin sensitivity, and selection on PLET agar, but may require a laboratory environment and 24 to 48 h to complete. Quicker and more portable identification methodologies may include ELISA and molecular (PCR) techniques; however, the antibody test may require large cell numbers and may cross react with other *Bacillus* species, while PCR, although specific, may not discriminate between live and dead organisms.

The lysogenic Wβ phage may have desirable and/or necessary attributes for generating a specific *B. anthracis* reporter phage. First, it may have a very broad host range and has been shown to infect all (171 strains tested) *B. anthracis* non-encapsulated (rough) strains analyzed. Second, it may be 'specific' to *B. anthracis* species. For example, Wβ did not lyse 44 *Bacillus megaterium* strains, 10 *Bacillus pumilis* strains, 11 *Bacillus firmus* strains, 26 *Bacillus subtilis* strains, 28 *Bacillus mycoides* strains, 10 *Bacillus coagulans* strains, 3 *Bacillus licheniformis* strains, and 2 *Bacillus circulans* strains. Although Wβ has been shown to lyse a small number of *B. cereus* strains (e.g., 2 out of 54 *B. cereus* strains tested), the susceptible *B. cereus* strains are classed as "atypical" *B. cereus*. These strains are monomorphic to *B. anthracis* at multiple allozyme loci and are generally described as *B. anthracis* representatives cured of its virulence plasmids. Third, Wβ has recently been sequenced making genetic modification feasible. Moreover, the lytic variant γ phage, which evolved from the Wβ parental strain, is routinely used by the CDC and various public health labs in the U.S. as a diagnostic standard for the identification of *B. anthracis*.

The *Vibrio harveyi* luxAB 'light' genes may be used as a reporter genes since: (i) the luxAB genes have been successfully used as a reporter signal for the phage-mediated detection of *Listeria, Salmonella*, and *Mycobacteria*; (ii) the light signal may be visualized by a simple hand-held luminometer; (iii) no processing of the sample is required; the only requirement is the addition of the substrate n-decanal, and (iv) active metabolism is required for luxAB expression and light production. Thus, viable cells produce a light signal, which will allow the detection system to distinguish live (potentially infectious) and dead cells. This is a distinct advantage over PCR detection methodology which may detect the presence of the *B. anthracis* virulence plasmid, but yields no information as to whether the cells are potentially infectious.

Integrating luxAB reporter genes into the Wβ genome may produce a viable phage capable of producing light following *B. anthracis* infection.

Figure 13:
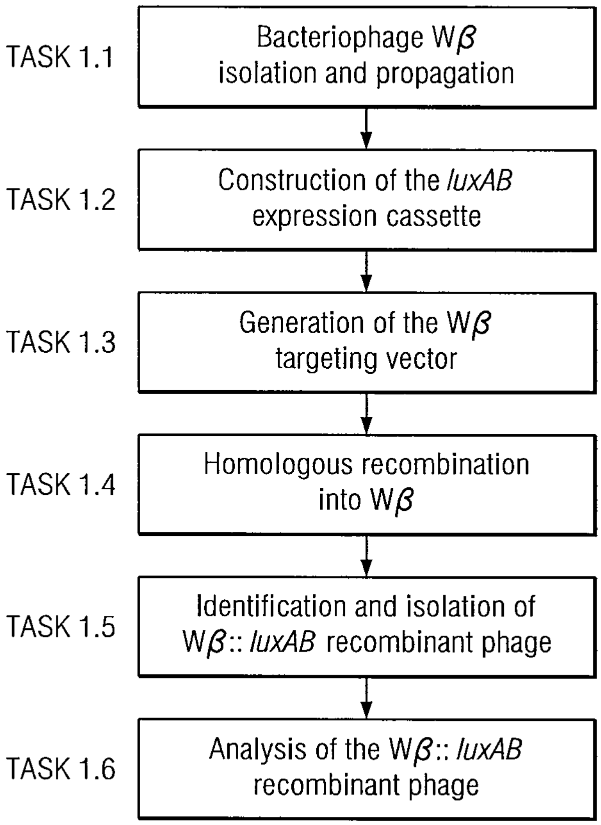
FIG. 13 is a flow diagram of a process for generating a *B. anthracis* luxAB reporter phage in accordance with an embodiment of the disclosure.

The following 6 tasks may be performed to generate a *B. anthracis* luxAB reporter phage (FIG. 13). Task 1.1 may include isolating and propagating *B. anthracis* Wβ phage. Task 1.2 may include generating a luxAB expression cassette under the transcriptional and translational control of preferred *Bacillus* expression sequences. Task 1.3 may include cloning and constructing a homologous recombination cassette which will target luxAB to a non-essential region of the Wβ genome. Task 1.4 may include integrating the luxAB cassette into the Wβ genome. Task 1.5 may include identifying and isolating recombinant Wβ::luxAB phage by the ability of infected cultures to emit light. Task 1.6 may include verifying luxAB integration by diagnostic agarose gel electrophoresis and PCR, and analyzing the 'fitness' of the recombinant phage compared to the wild-type phage.

Example 17A

Bacteriophage Wβ Isolation and Propagation

The *B. anthracis* Wβ lysogenic phage, which does not contain antibiotic resistance modules (unlike γ), may be isolated and induced from its prophage state using a similar methodology described by Schuch & Fischetti. The lysogenic *B. cereus* ATCC11950 strain (containing predominantly Wβ and a rare α phage) may be grown on brain heart infusion (BHI) agar plates containing 20 μg/ml of fosfomycin. The presence of fosfomycin may produce 'donut-shaped' colonies containing phage in the center. The center clearing zones of 20 colonies may be picked with sterile tips, pooled, mixed with SM buffer (50 mM Tris-HCl [pH7.5], 0.1M NaCl, 8 mM $MgSO_4.7H_2O$, 0.01% gelatin) and passed through a 0.22 μm membrane filter to remove bacteria.

The phage (mostly Wβ) may be propagated and enumerated using the "atypical" *B. cereus* RSVF1 (ATCC4342). *B. cereus* RSVF1 and *B. anthracis* are monomorphic at multiple allozyme loci, and share similar phenotypic features such as lack of motility, matt colony morphology and filamentous structure. *B. cereus* RSVF1 is one of the few non-*B. anthracis Bacillus* species that is susceptible to Wβ and γ phage. *B. cereus* RSVF1 may be prepared by growing the cells in BHI media at 30° C. until an $OD_{600}$ of 0.6 is reached. The cells may be harvested by centrifugation at 4,000×g for 10 min and resuspended in BHI to an $OD_{600}$ of 2.0. Cells (100 μl) may be mixed with an equal volume of the phage preparation and incubated at room temperature for 10 min to allow pre-absorption of the phage to the bacteria. A low MOI (multiplicity of infection) may be used to select for cells that are infected by a single phage using the agar overlay method. The phage/bacteria mixture may be added to pre-warmed (47° C.) 'molten' BHI containing 0.7% agar, mixed gently, and poured over pre-warmed BHI agar plates. The plate may be left on the bench until the agar solidifies, and then incubated upside down at 30° C. overnight. After overnight incubation, the presence of turbid plaques will indicate lysogenic phage are present.

To generate phage stocks, 4 distinct clonal plaques may be picked with a sterile Pasteur pipette and propagated on *B. cereus* RSVF1. Briefly, early exponential phase cells (10 ml cultures) in BHI media at 30° C. may be individually inoculated with the plaques. After overnight growth, the cultures may be centrifuged and the supernatants passed through a 0.22 μm filter. The phage stocks may be enumerated on *B. cereus* RSVF1 using the agar overlay technique. To ensure the phage stocks contain Wβ and not a phage, the phage may also be enumerated on the Wβ prophage strain (ATCC11950); a Wβ preparation may not be able to superinfect this strain.

Example 17B

Construction and Design of a luxAB Expression Cassette

LuxA and luxB may be PCR-amplified using the proof-reading thermostable enzyme PfuUltra (Stratagene) and pQF110 (ATCC77113, contains luxAB) as template. The PCR primers may be designed to contain XbaI BamHI and HindIII/XhoI, respectively, for directional cloning into the corresponding sites of pBluescriptSK$^-$ (Stratagene). The 5' primers may contain a consensus ribosome binding site (e.g., TAAGGAGGTAAAAAA(ATG); SEQ ID NO:2) which has been shown to mediate efficient translation initiation in Gram-positive species such as *Staphylococcus aureus, Enterococcus faecalis*, and *Enterococcus faecium*. The luxA and luxB may be sequentially cloned into pBluescriptSK$^-$ (to create pluxABSK$^-$) by standard cloning methodology, and transformed into the propagating strain *E. coli* ER2738. Diagnostic restriction endonuclease analysis and agarose gel electrophoresis may be used to verify that the correct clone has been selected. The sequence of the PCR-amplified luxA and luxB genes may be verified by deoxy dye terminator sequencing.

Figure 14:
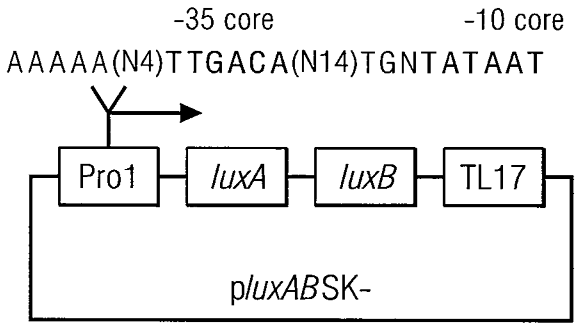
FIG. 14 is a schematic of the luxAB expression cassette and Pro1 (AAAAATTGACATGNTATAAT (SEQ ID NO. 3) conserved nucleotides (arrow denotes the direction of transcription)

A designed *Bacillus* promoter (Pro1) may be used to drive luxA and luxB expression. The promoter may be designed based upon compilation and analysis of 236 promoters recognized by the *B. subtilis*, and other Gram-positive RNA polymerases. The Pro1 promoter may contain the following conserved elements/nucleotides: (i) the −35 (TTGACA) (SEQ ID NO. 4) and −10 (TATAAT) (SEQ. ID. NO. 5) hexanucleotide core elements; (ii) a TG (SEQ ID NO. 6) dinucleotide at positions, −15 and −14, and (iii) 5 A residues upstream of the −35 region. The designed promoter may be functional in both *B. cereus*, and *B. anthracis*, and be highly expressed. A similarly designed promoter was highly expressed in other Gram-positive species (8. *aureus, E. faecalis*, and *E. faecium*) bacteria. ProI may be cloned upstream of luxA and luxB into the Sac I/Not I sites. To ensure efficient processing and to prevent runaway transcription, the transcriptional terminator TL17 may be cloned downstream (KpnI sites) of the luxA and luxB genes (FIG. 14). The identity of the Pro1 and TL17 sequences may be verified by deoxy dye terminator sequencing.

Example 17C

Generation of the Wβ Targeting Vector for Homologous Recombination

One of the major differences between lysogenic Wβ and the lytic variant is that the 2,832 bp locus encoding wp40 and wp41 has been deleted in γ and replaced by a 1,360 bp fosfomycin resistance module (use of γ phage outside of the lab therefore, comes with the risk of the potential transfer of the γ antibiotic resistant module to infected *Bacillus* strains by phage-mediated gene flow which is undesirable). Although the functions of Wp40 and Wp41 proteins are unknown, both proteins do not play an essential role in phage propagation. Therefore, integration of the luxAB expression cassette may be targeted to the wp40 and wp41 locus of Wβ. The wp40 and wp41 genes may be replaced by the ~2,200 bp luxAB cassette by homologous recombination based on a double cross over event. Replacement, rather than insertion, will ensure that the size of the phage genome will not increase, thereby reducing the risk of producing defective phage.

Wβ DNA may be isolated from the clarified lysates using a commercially available phage DNA isolation kit (Qiagen #12523). A 600 bp fragment encompassing wp41 and wp41/wp42 intergenic fragment (3' flanking sequences, nucleotides 35,800 to 36,300; Genbank accession number DQ289555) may be PCR-amplified using Wβ DNA as template and cloned into the SalI/EcoRI sites of pHP13 (*Bacillus* Genetic Stock Center, ECE32). pHP13 is a multicopy *E. coli/B. subtilis* shuttle vector containing an adequate multiple cloning site and the chloramphenicol acetyltransferase gene for antibiotic selection. A 600 bp wp39/wp40 fragment (encompassing 33,000 to 33,600 bp of the Wβ genome) may be PCR-amplified and cloned into the HindIII/SalI sites of the above vector. The luxAB expression cassette may be then be cloned into the internal SalI site, and may therefore be flanked by the Wβ DNA to create pluxABHP13.

To analyze whether the luxAB expression vector is functional and produces light in *Bacillus*, the "atypical" *B. cereus* RSVF1 strain may be transformed with the pluxABHP13 plasmid. *B. cereus* RSVF1 may be electroporated with pHP13 (control plasmid) and pluxABHP13 as described previously and transformants may be selected on BHI agar supplemented with 5 μg/ml chloramphenicol. The resulting colonies may be examined under dark field illumination using the Chemodoc XRS gel documentation system (performed at the Medical University of South Carolina, (MUSC)) in the presence of the substrate decanal. Luminescent colonies may not be obtained for the control *B. cereus* strain harboring the empty control plasmid (pHP13); however, luminescent colonies may be readily evident for *B. cereus* harboring pluxABHP13. This may indicate that *B. cereus* is successfully transformed with a functioning luxAB cassette. Similar experimental procedures have been performed for the generation of a luxABM13 filamentous phage for *E. coli* detection.

A luxAB expression cassette may be also or alternatively targeted to a phage lysogeny module (e.g., wp28 and wp29). Wp28 and wp29 are also non-essential for phage function, and provides another location for engineering phage. If multiple locations yield functional phage, it may be desirable to select the engineered phage that is the most stable (e.g., does not shed the luxAB genes) and is most suitable for a biosensor.

Example 17D

Homologous Recombination

Figure 15:
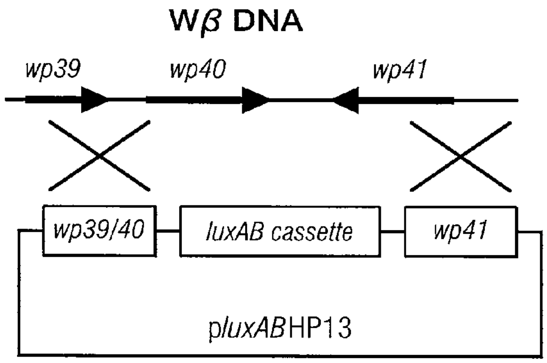
FIG. 15 is a schematic of the *Bacillus* shuttle vector and homologous recombination process leading to integration of the luxAB expression cassette by a replacement/double crossover event in accordance with an embodiment of the disclosure.

A strategy involving direct cloning into the Wβ genome may not be pursued since the genome is large (40,864 bp) making cloning difficult, and/or because it may lack appropriate restriction endonuclease sites. Therefore, homologous recombination between phage and plasmid DNA based on a double crossover event may be used to integrate luxAB into the phage genome (FIG. 15). To allow for multiple rounds of phage propagation, Wβ may be introduced into *B. cereus* RSVF1 harboring pluxABHP13 by phage infection using the agar overlay technique. Following infection and overnight growth, phage from multiple plates exhibiting confluent lysis may be eluted with 10 ml of SM buffer and filter sterilized. The titer of the phage lysates may be determined.

Example 17E

Identification of Recombinant Wβ::luxAB Phages

Wβ::luxAB phage may be identified and isolated by a similar strategy used for the generation of *Listeria*-specific luxAB recombinant phage. Phage lysates, containing predominantly wild-type Wβ and a very small number of Wβ::luxAB phages, may be used to infect *B. cereus* RSVF1 using the agar overlay technique with the following modifications: (i) 24×24 cm Petri dishes may be used instead of the 'standard' 10×15 cm to allow more plaques to be screened per plate, and (ii) a high number of phage may be used for infection in combination with a short (10 h) overnight incubation to allow for the maximum number of small and nearly confluent turbid plaques per plate. Infection and screening may be performed at MUSC (contract work). Up to 25 plates may be screened, each containing ~3,000 to 5,000 plaques per plate. The plates may be screened immediately following the addition of decanal vapor (2 μl placed on the lid of the dish) under dark field illumination using the Chemodoc XRS gel documentation system. The frequency of integration may be approximately $5\times10^{-4}$ i.e., one lux phage per 50,000 wild-type particles. Therefore, only 1 to 2 plates may contain a small, but detectable light signal. Turbid plaques from lux-ABM13-infected *E. coli* may be used as a positive control (section 9, related research). Phage from the positive plates may be eluted with 20 ml of SM buffer, filter sterilized and used for infection of *B. cereus* RSVF1 using the agar overlay technique. This screening process may be repeated until distinct individual turbid plaques emitting a bioluminescent phenotype can be picked and isolated. High titer Wβ::luxAB lysates may be prepared as described in Task 1.1.

Prophetic Example 18

Analysis of the Ability of Wβ::luxAB to Detect *B. anthracis*

For Wβ::luxAB to function efficiently and detect *B. anthracis*, there are a number of parameters which may be analyzed and optimized. Infectious and/or weaponized forms of *B. anthracis* spores may be used by a bioterrorist. Therefore, it may be desirable to demonstrate detection of spores. In addition, the ability to detect: (i) viable, infectious spores only, and (ii) different spore concentrations (sensitivity and dose response) and the signal response time may be analyzed. Furthermore, since Wβ::luxAB may be used for the detection of *B. anthracis* under diverse environmental conditions, it may be desirable and/or essential that: (i) the phage are stable for extended storage periods under standard conditions; (ii) the phage remain infective over a range of pH and temperatures, and/or (iii) the Wβ::luxAB infected cultures produce a stable light signal over a range of temperatures. For screening purposes, it may be desirable to analyze the effectiveness of Wβ::luxAB using an attenuated *B. anthracis* strain (rather than an infectious strain) (e.g., to better accommodate safety and regulatory concerns).

Wβ::luxAB may be a stable phage that can sensitively and quickly detect the presence of *B. anthracis* spores by emitting a bioluminescent signal.

Figure 16:
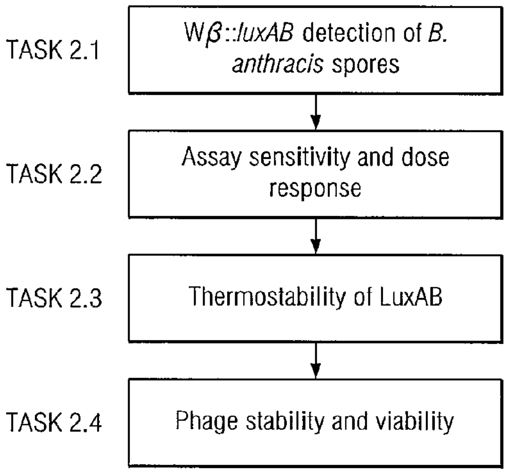
FIG. 16 is a flow diagram of a process for analyzing the effectiveness of a phage-mediated detection system in accordance with an embodiment of the disclosure.

The following 4 tasks may be performed to analyze the effectiveness of the phage mediated detection system (FIG. 16). Task 2.1 will generate *B. anthracis* spores and analyze the utility of the detection system when used in conjunction with spore germinating agents. In addition, spores and vegetative cells may be heat killed and examined for the inability of the phage detection system to exhibit a positive response (light signal). Task 2.2 will infect varying concentrations of germinating spores to examine the sensitivity limits of detection, the dose-response characteristics, and the signal detection time. Task 2.3 will examine the thermal stability of the bioluminescent signal in *B. anthracis*. Task 2.4 will determine the ability of Wβ::luxAB to retain infectivity at different pH's, at different temperatures, and over extended storage periods.

Example 18A

Assay Sensitivity and Dose Response

The ability to detect low concentrations of spores and to relatively quantify the number of spores present are important characteristics of a detection methodology. Previous studies have demonstrated that a luxAB-tagged *Listeria* phage was able to detect 500-1000 *Listeria* CFU/ml after a 2 h incubation. Following an enrichment step however, the phage could detect as few as 1 *Listeria* cell per gram of artificially contaminated salad.

To investigate assay sensitivity and dose-dependent characteristics, a ten-fold serial dilution of spores ranging from $1\times10^{8}$ to $1\times10^{1}$ may be incubated under germination inducing conditions and infected with $1\times10^{9}$ Wβ::luxAB plaque forming units (PFU) as described above. Since an MOI of at least 10 may be used (MOI increases as the spore number decreases), every cell may be infected. The results may demonstrate that as the number of spores decreases, bioluminescence decreases proportionally indicating dose-response characteristics. By performing a dose response curve in relation to bioluminescence (and time of response), a standard curve may be produced which may enable the relative quantification of the number of spores in an unknown sample.

The lowest number of detectable spores may be determined. As the number of spores decreases, the signal response time is also expected to decrease. The sensitivity of the assay may be similar to previous phage-based studies (500-1,000 CFU/ml) but may depend on the efficiency of infection, expression of the luxAB expression cassette, and the sensitivity of the luminometer. Although the infectious dose for GI anthrax in humans is unknown, rhesus monkeys infected with $10^{8}$ spores do not develop an infection. Therefore, the human infective dose is likely to be at least $10^{8}$ spores, if not higher, since monkeys are considered to be more susceptible to anthrax than humans. Consequently, the sensitivity of the Wβ::luxAB assay may be orders of magnitude higher than the human infectious dose.

Example 18B

LuxAB Expression and Stability at Different Temperatures

Previous studies have demonstrated that the LuxAB proteins are unstable at temperatures above 30° C. Although spore germination and bioluminescence assays may be performed at lower temperatures (22° C.), LuxAB thermostability may also vary depending on the host species. Therefore, to investigate LuxAB thermostability in *Bacillus* independently from infection and spore germination, *B. anthracis* Sterne may be grown in BHI media at 30° C. Exponentially growing vegetative cells (~$1\times10^{7}$ CFU/ml) may be infected with Wβ::luxAB (~$5\times10^{8}$ PFU/ml). The culture may be incubated at 30° C. for 10 min to allow phage absorption to the cells, and then divided equally and incubated at various temperatures (10, 15, 20, 25, 30, and 35° C.). Bioluminescence may be monitored every 10 min. Since temperature changes may also influence rates of luxAB expression (transcription and translation), changes in bioluminescence may not be strictly correlated with LuxAB stability. If warranted, a translation inhibitor may be added to the cultures 30 min post infection to prevent further LuxAB protein synthesis, and ensure only preformed LuxAB mediated luminescence may be detected. Nevertheless, the experiment should provide an indication of LuxAB thermostability in *B. anthracis* Sterne.

Example 18C

Phage Stability and Viability

An aspect of whether a phage (e.g., a Wβ::luxAB phage) may be suitable for *B. anthracis* detection may be whether the lysates will remain stable after long-term storage and remain infective under the diverse conditions that may be encountered outside the laboratory. Ideally, a phage may be resistant to changes in: (i) pH values; (ii) temperature, and (iii) light exposure. In general, phage are extremely stable and can survive a range of pH's (pH 4-10) and temperatures (up to 60° C.). Specific studies on *B. anthracis* phage have demonstrated that phage remained viable at temperatures ranging from −20 to 37° C. but were sensitive to temperatures over 55° C. In addition, the Wβ lytic variant γ, was shown to be stable exhibiting less than a $\log_{10}$ drop in viability after 1-2 years storage at 4° C. The latter study also recommended *B. anthracis* CDC684 for the production of stable and high titer lysates. Although it is very likely that Wβ and γ will exhibit similar stability properties, it is unknown what effect, if any, the introduction of the luxAB expression cassette has on the fitness of Wβ. Prior to determining phage stability, Wβ::luxAB may be concentrated and purified using polyethylene glycol (PEG). 0.75M NaCl may be added to the phage lysates and mixed continuously at 4° C. for 1 h to dissociate the phage from the bacterial debris and media components. 10% PEG 8000 may be added gradually, and the phage may be allowed to precipitate at 4° C. overnight. The precipitated phage may be collected by centrifugation (11,000×g, 15 min, 4° C.) and resuspended gently in SM buffer.

To determine the stability of Wβ::luxAB at different pH's, the pH of SM buffer may be adjusted to the following values using 1M NaOH or 1M HCl: pH 2, 4, 6, 8, 10, and 12. The purified Wβ::luxAB suspension (approx. $1\times10^{10-11}$ PFU/ml) may be diluted 1/200 into pH-adjusted SM buffer and stored at ambient temperature or at 4° C. Both ambient and cold temperatures may be tested since stability at different pH's is influenced by different storage temperatures. After 24 h incubation at the designated temperatures, the number of phage may be titered using the agar overlay technique and compared to the number of viable phage in the original starting sample. Wβ::luxAB may remain viable over a range of pH values.

Since Wβ::luxAB may be used outside of the lab after months (if not years) of storage, it may be desirable for the phage to remain viable under 'standard' conditions. To determine the stability of phage preparations under different storage conditions, purified phage lysates may be stored in SM buffer in the dark at 4° C., room temperature (approx. 19° C.), and 37° C. for the duration of the grant period. Phage aliquots (100 μl) may be enumerated for plaques using the agar overlay technique after 1, 2, 3, and 4 months (and longer if possible) and compared to the original titer. Wβ::luxAB may be evaluated for its ability to remain viable at different temperatures, and over long time periods. Since many phage species are stable after freeze-drying in the presence of a cryoprotectant such as trehalose, phage according to some embodiments of the disclosure may be freeze-dried.

The environmental conditions favoring the Wβ lysogenic or lytic mode of growth are unknown. Consequently, experiments varying temperature, MOI, and bacterial inoculum may alter the frequency of lysogenic conversion. This in turn may alter bioluminescence activity independent of the variable being analyzed. Therefore, care may be taken to ensure results are not misinterpreted.

Quick and efficient spore germination may be desirable for the effectiveness of the detection system. Samples from suspected food may be analyzed on site under conditions conducive to spore germination and phage infection/replication using a hand held illumination device. However, a positive 'bioluminescent' signal may not be obtained if the spores are viable but non culturable (VBNC). Under these conditions, VBNC spores will not germinate and will go undetected but are still potentially infectious. Nonetheless, the frequency of occurrence of VBNC spores may be very low.

The Wβ and γ phage have an extraordinary ability to infect most *B. anthracis* strains. Apparently, only 2 *B. anthracis* strains have been identified as γ resistant. Without being limited to any mechanism of action, the reason why the phage can infect most *B. anthracis* strains may be due to the lack of diversity among *B. anthracis* strains which has been attributed to the lack of opportunities to grow, infect, and evolve compared to other bacterial species. A potential caveat of the phage detection system, however, is the potential to infect and detect a small number of "atypical" *B. cereus* strains. *B. cereus* are a potential 'natural' contaminant on food, and are estimated to cause 0.5% of all bacterial foodborne related disease cases. Therefore, although Wβ::luxAB will infect the "atypical" *B. cereus* strain, the luxAB promoter may not be expressed and light may not be produced. To circumvent this possibility, some embodiments of the disclosure may include identifying and fusing a *B. anthracis* specific promoter to luxAB.

Prophetic Example 19

An approach for detecting (and killing) *B. anthracis* utilizes purified phage lysins, which when added to the bacteria, causes rapid lysis. ATP is released from the lysed cell, and when mixed with luciferin/luciferase, emits a light signal. A disadvantage of this product may be a dependence on production of purified enzymes, which may be labile and/or expensive. A Wβ::luxAB phage that can specifically detect and kill a desired microorganism may be desirable alternative according to some embodiments.

Prophetic Example 20

Food safety is an established market worldwide. Products in this industry satisfy the need for safe consumables which is a continually renewable market. In a 2006 market report published by Freedonia (Food Safety Products to 2010, Study #2051), the food safety market is $1.6 billion in the U.S. and growing at an annual rate of 5.5%. A similar phage-based approach for the eradication of *Listeria* (Intralytix) on 'ready to eat foods' has recently been approved by the FDA. In addition to food safety, a phage detector according to some embodiments, may directly benefit the public following an anthrax attack. Some embodiments of the disclosure may be used to detect and decontaminate anthrax contaminated buildings, offices, planes, ships, and trains. Some embodiments of the disclosure may also be used to monitor the efficiency of chemical decontamination.

Some embodiments of the disclosure may be able to both detect and subsequently kill *B. anthracis*. Some embodiments of the disclosure may be: (i) cheap to produce; (ii) specific for *B. anthracis*; (iii) discriminatory between viable and non-viable cells; (iv) non-toxic (with the proviso of the LuxAB substrate, decanal), and/or (v) portable (not lab based). A system may be used, for example, to both detect and decontaminate anthrax.

Example 21

Construction and Design of a luxAB Expression Cassette

A 'bioluminescent' phage capable of specifically infecting and transducing a bioluminescent phenotype to *Bacillus anthracis*, the causative agent of anthrax, was generated. The recombinant Wβ::luxAB *B. anthracis* 'bioluminescent' phage was generated by integrating the *Vibrio harveyi* luxA and luxB genes into a non-essential region of the Wβ phage genome. This resulted in a phage that was capable of specifically infecting and conferring a bioluminescent phenotype to *B. anthracis*. The Wβ::luxAB phage, when incubated in the presence of *B. anthracis* vegetative cells, resulted in a bioluminescent signal 12-16 min after infection. In addition, the Wβ::luxAB phage was able to confer a bioluminescent phenotype to *B. anthracis* germinating spores within 60 min after infection. Collectively, the results demonstrate that the Wβ::luxAB phage may be used as a *B. anthracis* detection system.

The *Vibrio* harveyi luxA and luxB genes were PCR-amplified using pQF110 (ATCC 77113) as template. The PCR primers were designed to contain XbaI/BamHI and HindIII/XhoI, respectively, for directional cloning into the corresponding sites of pBluescript-SK$^-$ (Stratagene). The 5' primers contained a consensus ribosome binding site (TAAGGAGGTAAAAAA(ATG); SEQ ID NO. 2) which has been shown to mediate efficient translation initiation in Gram-positive species. The luxA and luxB were sequentially cloned into pBluescript-SK$^-$.

A promoter was cloned upstream of luxA and luxB into the SacI/NotI sites. The "*Bacillus*" promoter was designed to contain a consensus −35 region, a 1 bp mismatch at the −10 region, 2 conserved A nucleotides 3' of the −1, and a SalI site at the 5' end to facilitate downstream cloning. To ensure efficient processing and to prevent runaway transcription, the transcriptional terminator TL17 was cloned downstream (KpnI sites) of the luxA and luxB genes. The luxAB cassette was flanked by SalI sites to facilitate subsequent cloning into the *E. coli/Bacillus* shuttle vector.

Example 22

Generation of the Wβ Targeting Vector for Homologous Recombination

Integration of the luxAB expression cassette was targeted to the wp40 and wp41 locus of Wβ. The wp40 and wp41 genes were targeted to be replaced by the ~2,200 bp luxAB cassette by homologous recombination based on a double cross over event. Replacement, rather than insertion, was preferred since the size of the phage Wβ genome would not increase, thereby reducing the risk of producing defective phage.

Figure 17:
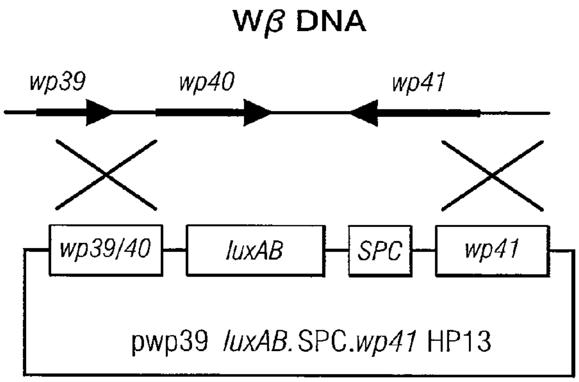
FIG. 17 is a schematic of the *Bacillus* shuttle vector and homologous recombination process leading to integration of the luxAB expression cassette by a replacement/double crossover event in accordance with an embodiment of the disclosure.

A 375 bp fragment (5' flanking sequences) encompassing the wp39/wp40 intergenic region and the 5' end of wp40 (5' flanking sequences, position 33,312 to 33,686; GenBank accession number DQ289555) was PCR-amplified using Wβ DNA as template. A 385 bp wp41 region (encompassing 35,948 to 36,331 bp of the Wβ genome) was also PCR-amplified corresponding the to the 3' end of the recombination cassette. The wp39/wp40 and wp41 primers were designed to incorporate HindIII/SalI and SalI/EcoRI restriction sites, respectively at the 5' and 3' ends to facilitate subsequent cloning into pBluescript-SK$^-$. The wp39/wp40 and the wp41 Wβ phage DNA was then excised with HindIII/SalI or SalI/EcoRI, respectively, and cloned into the corresponding sites of the *E. coli/Bacillus* shuttle plasmid pHP13 (*Bacillus* Genetic Stock Center, catalog #ECE32). By cloning wp39/wp40 and wp41 into the HindIII/SalI or SalI/EcoRI, respectively, a unique internal SalI site was available. Consequently, the luxAB expression cassette was then cloned into the internal SalI site, and was therefore flanked by the Wβ DNA at the 5' and 3' ends to create pwp39.luxAB.wp41.HP13. To provide a positive selection pressure for recombinant phage isolation, the spectinomycin (SPC) antibiotic resistance gene was PCR amplified from plasmid pDG1728 (*Bacillus* group stock center ECE114) and inserted into the recombination cassette 3' of the luxAB genes to create pwp39.luxAB.SPC.wp41.HP13 (FIG. 17).

Example 23

Homologous Recombination and Recombinant Wβ::luxAB Phage Isolation

Homologous recombination between phage and plasmid DNA based on a double crossover event was used to integrate luxAB into the phage genome. To allow for multiple rounds of phage propagation, the *B. cereus* RSVF1 Wβ lysogen was electroporated with pwp39.luxAB.SPC.wp41B.HP13 and transformants were selected for by growth on BHI agar plates supplemented with 100 μg/mL SPC. All the transformants were positive for bioluminescence as expected. Single colonies were grown in BHI/SPC at 30° C. for 18 h and the resulting cultures were clarified by centrifugation (10,000×g, 3 min) and the supernatants passed through a 0.22 μm filter. The resulting phage supernatants were expected to contain mostly wild-type Wβ phage and if a double crossover recombination even had occurred, a small number of recombinant Wβ::luxAB phage. The phage supernatants were treated with DNase I (20 units, 30° C., 30 min) to digest contaminating plasmid DNA. The resulting phage preparation was used to infect *B. cereus* RSVF1 and plated onto BHI/SPC agar plates in order to select and isolate *B. cereus* Wβ::luxAB lysogens. After overnight growth at 30° C., 6 SPC resistant *B. cereus* colonies were obtained.

Example 24

Verification of the Wβ::luxAB Recombinant Phage

Figure 18:
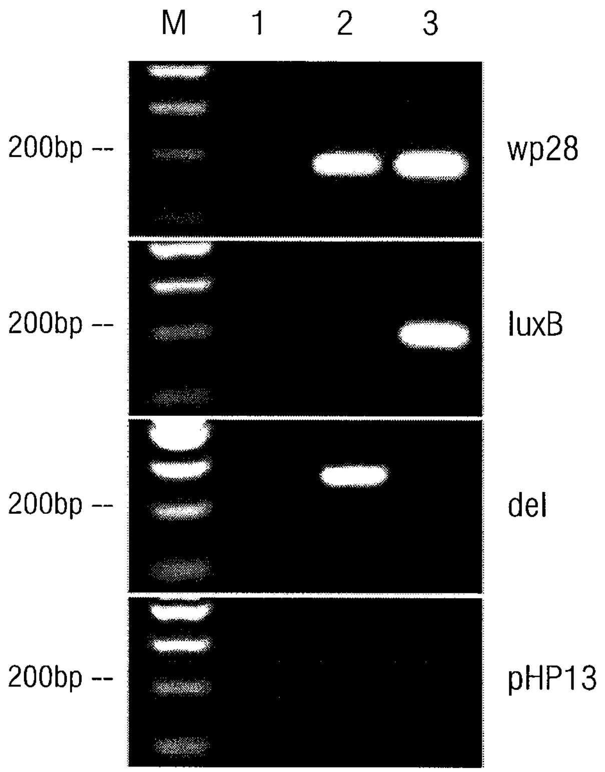
FIG. 18 shows size-fractionated PCR products resulting from amplification of cell-free phage supernatants confirming the presence of recombinant Wβ::luxAB phage in accordance with an embodiment of the disclosure.

To confirm that integration was accomplished through a double crossover replacement event, and to verify the presence of Wβ::luxAB recombinant phage, cell-free phage supernatants were analyzed by PCR for the presence of wp28 (Wβ DNA), luxB, the absence of plasmid backbone (pHP13), and the absence of the specific Wβ sequence (DEL) which was expected to be replaced by the double crossover replacement event. PCR analysis of the Wβ::luxAB for the presence of wp28 and luxB produced the PCR products of the correct predicted sizes, and no products were generated using primers specific for the recombination plasmid backbone (pHP13) or for the Wβ sequence (DEL) expected to be replaced by the double crossover replacement event. Results are shown in FIG. 18. PCR analysis was performed in the absence of template (lane 1), with the wild-type Wβ phage (lane 2) or with the recombinant Wβ::luxAB phage (lane 3). The predicted PCR product sizes for wp28, luxB, del and pHP13 were 178, 184, 258, and 208 bp, respectively. PCR analysis of the recombinant phage was positive for the luxB and wp28 as expected, and negative for the segment which was predicted to be deleted (del), and negative for the plasmid backbone. In addition, plasmid preparations from the putative *B. cereus* lysogens did yield detectable plasmid DNA. Therefore, the results strongly suggested the presence of Wβ::luxAB phage DNA.

Figure 19:
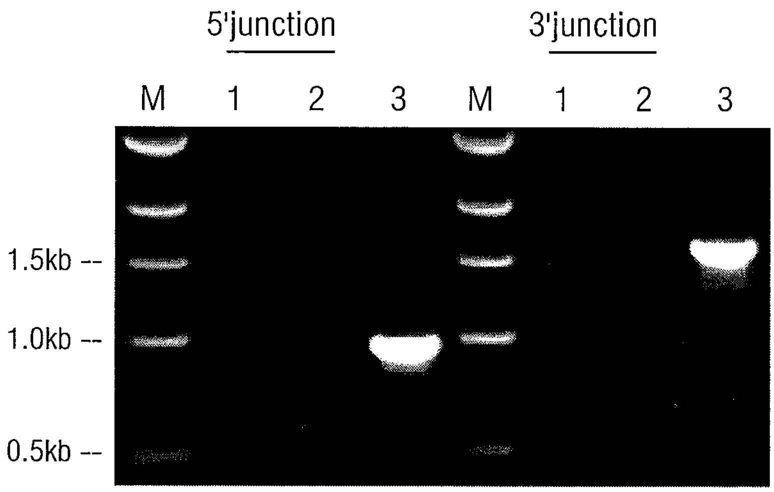
FIG. 19 shows size-fractionated PCR products resulting from amplification of cell-free phage supernatants confirming correct integration of luxAB into the Wβ genome in accordance with an embodiment of the disclosure.

To analyze whether the luxAB integration into Wβ had occurred at the correct (predicted) site in the Wβ genome, primers were designed to span either the 5' or 3' integration junctions; each primer set was designed with one primer binding within the luxAB recombination cassette and one primer binding external to the recombination cassette. Results are shown in FIG. 19. PCR analysis was performed in the absence of template (lane 1), with the wild-type Wβ phage (lane 2) or with the recombinant Wβ::luxAB phage (lane 3). The predicted size of PCR products for the 5' junction and 3' junction were 988 and 1641 bp, respectively. PCR analysis using the 5'-INT and 3'-INT primers generated PCR products of the correct predicted size. These results indicated that the luxAB cassette had integrated into the Wβ genome at the correct predicted site. In addition, since DNase 1-treated cell free phage supernatants (after passing through a 0.22 μm filter) were also able to transduce a bioluminescent phenotype to *B. anthracis* Sterne, these results collectively indicated that intact recombinant Wβ::luxAB phage were generated.

Example 25

Wβ::luxAB Detection of *B. anthracis* Vegetative Cells

Figure 20:
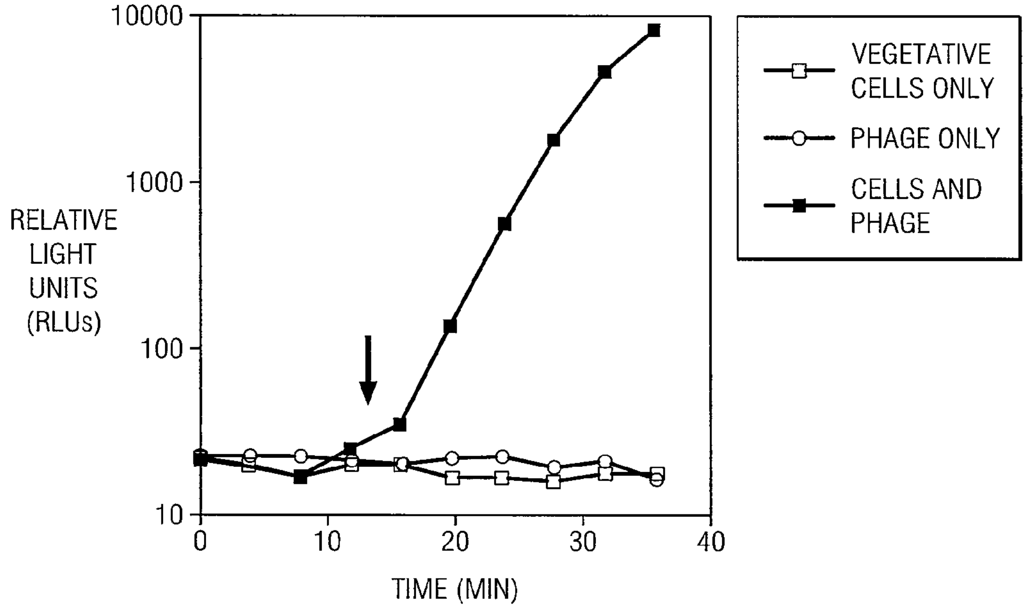
FIG. 20 shows a plot of bioluminescence (relative light units) over time observed for Wβ::luxAB-infected *B. anthracis* vegetative cells in accordance with an embodiment of the disclosure.

The signal response time of Wβ::luxAB to transduce a bioluminescent phenotype to *B. anthracis* vegetative cells was assessed. Exponentially growing *B. anthracis* ($OD_{600}$ of approximately 0.7, $1\times10^8$CFU/mL) was mixed at 30° C. with an equal volume of phage ($6\times10^3$ PFU/mL, a final multiplicity of infection (MOI) of ~0.0001) at time zero (0) and the ability of Wβ::luxAB to transduce bioluminescence was monitored over time using a Biotek Synergy II multiplate detection reader. A steady increase in bioluminescence was detected from *B. anthracis* phage-infected cells (FIG. 20). Moreover, a detectable light signal above background (controls of phage alone, or cells alone) was evident 12-16 min after phage infection. Therefore, the results indicated that: (i) the Wβ::luxAB phage were able to infect and transduce a bioluminescent phenotype to *B. anthracis* vegetative cells; (ii) the luxAB genes were functional in *B. anthracis* and produced a steady detectable bioluminescent signal (over the time period analyzed), and (iii) the signal response time was quick at 12-16 min after phage infection (FIG. 20, arrow).

Example 26

Wβ::luxAB Detection of Germinating Spores

The results demonstrated that the recombinant Wβ::luxAB phage was able to quickly detect vegetative cells; however, *B. anthracis* spores are a transmissible and infectious form of anthrax. Therefore, it may be desirable to demonstrate the utility of the detection system by using spores as the starting material. Consequently, a single *B. anthracis* Sterne colony was grown overnight in BHI medium at 30° C. with vigorous shaking. Spores are formed under conditions of nutrient starvation. Therefore, spores were generated by diluting the overnight culture 1:10 in minimal media (0.5 mM $MgCl_2$, 0.01 mM $MnCl_2.4H_2O$, 0.05 mM $FeCl_3.6H_2O$, 0.05 mM $ZnCl_2$, 0.2 mM $CaCl_2$, 13 mM $KH_2PO_4$, 26 mM $K_2HPO_4$, 20 μg/ml L-glutamine, 1 mg/ml acid casein hydrolysate, 1 mg/ml enzymatic casein hydrolysate, 0.4 mg/ml yeast extract, and 0.6 mg/ml glycerol) and incubating at 30° C. with shaking. After 48 h, phase contrast microscopy indicated the presence of retractile spores; cultures consisted of >90% spores.

Cultures were centrifuged for 15 min at 3,000×g, washed 4 times with sterile $dH_2O$, and resuspended in 2 mL of $dH_2O$. Following a 30 min incubation at 70° C. (which kills the vegetative form only), the spores were washed 4 more times with $dH_2O$, with the uppermost layer of the pellet discarded after each wash. Spores were stored in $dH_2O$ at room temperature until used. Using phase contrast microscopy, the resulting suspension consisted of >99% spores; vegetative cells were not observed upon microscopic examination of multiple field of visions. Spores were enumerated by colony counting after 24 h growth at 30° C. on BHI agar plates and were determined to be a concentration of $3.3\times10^9$ CFU/mL.

Figure 21:
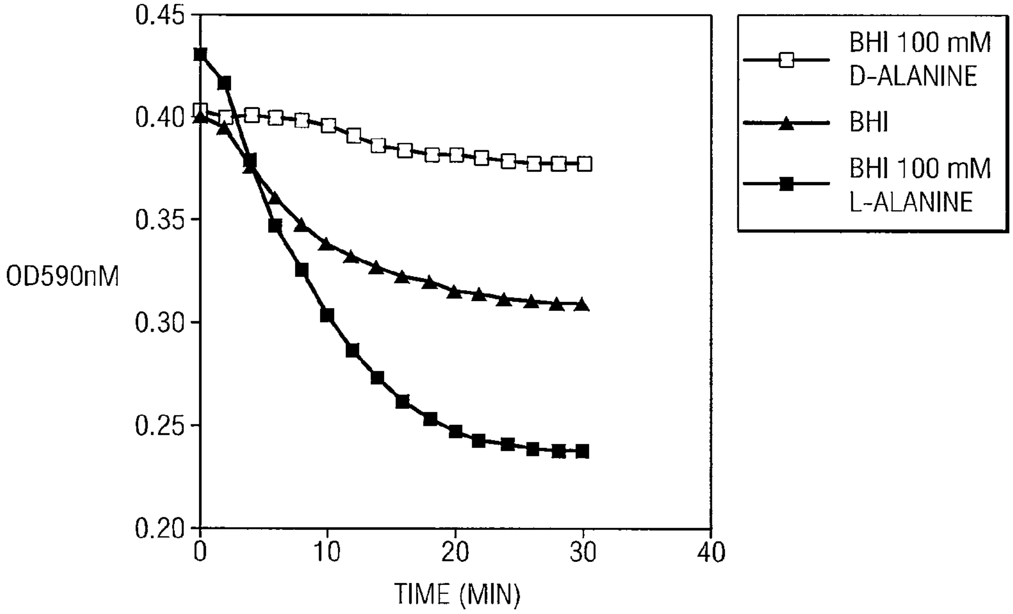
FIG. 21 shows a plot of *B. anthracis* spore germination ($OD_{590}$) over time at 35° C. in BHI media supplemented with the germination promoter (L-alanine) or inhibitor (D-alanine)
Figure 22:
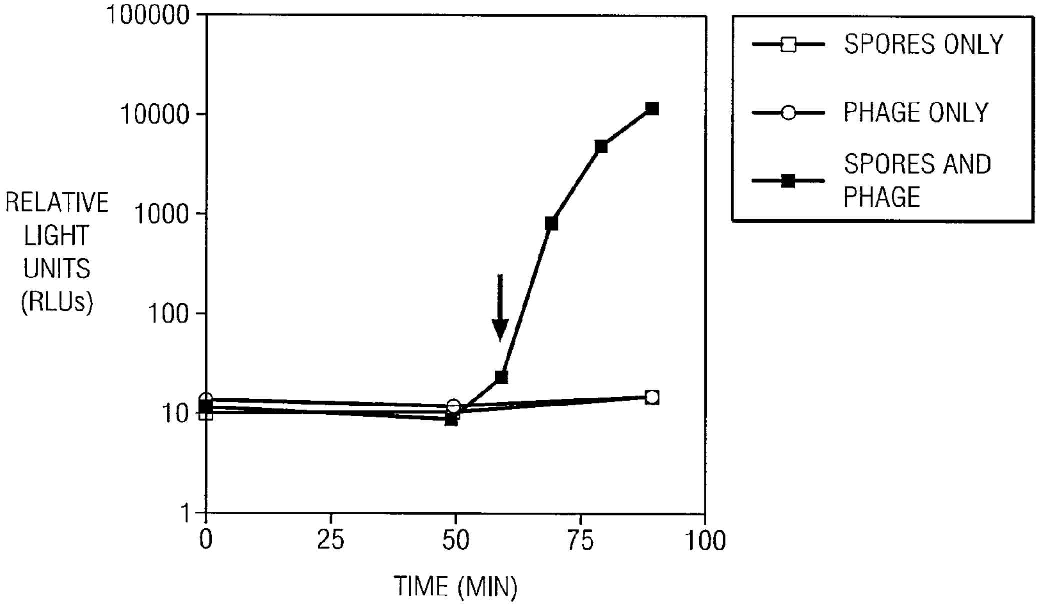
FIG. 22 shows a plot of bioluminescence (relative light units) over time observed for Wβ::luxAB-infected *B. anthracis* germinating spores in accordance with an embodiment of the disclosure.

*Bacillus* spores my be refractory to phage infection. This is most likely due to the phage receptor not being ‘available’ to binding on the spore surface. Therefore, the phage must be delivered under conditions that induce spore germination. *B. anthracis* spores are readily, and quickly germinated in BHI media (calf brain infusion solids, beef heart infusion solids, proteose peptone, glucose, sodium chloride, and di-sodium phosphate) supplemented with the amino acid L-alanine (100 mM) at 22° C. Spores are denser, and scatter light more strongly than the vegetative form. Consequently, germination can be assessed by looking for a decrease in optical density at 590 nm. Monitoring for a decrease in the retractile index is a common method used for analysis of spore germination. To examine the ability of *B. anthracis* Sterne spores to germinate, $8\times10^7$ CFU/mL of spores were resuspended in BHI, BHI supplemented with 100 mM L-alanine, or BHI supplemented with 100 mM D-alanine (germination inhibitor) and incubated at 35° C. As expected, spores incubated in BHI/L-alanine were quickly germinated (rapid decrease in the optical density within 15 to 20 min) while spores incubated in the presence of the inhibitor D-alanine displayed only a small decrease in the OD590 nm (FIG. 21). Next, the ability of Wβ::luxAB phage to infect and transduce a bioluminescent phenotype to *B. anthracis* spores was assessed in BHI with 100 mM L-alanine at 30° C. Spores ($1.6\times10^8$ CFU/mL) were heated at 65° C. for 30 min before infection (MOI of ~0.003). A detectable light signal above background (spores alone or phage alone) was observed after a 60 min incubation (FIG. 22, arrow). This suggests that the phage receptor is expressed and is accessible to phage binding on the cell surface within a short time period after spore germination. Collectively, the results demonstrated that Wβ::luxAB can effectively and quickly detect the presence of *B. anthracis* spores when used under conditions that promote spore germination. Since only germinating spores are infected, this also ensures that only viable, potentially infectious cells are detectable by the phage detection system.

Example 27

Assay Sensitivity

The ability to detect low concentrations of spores may be an important characteristic of a detection methodology. Previous studies have demonstrated that a luxAB-tagged *Listeria* phage was able to detect 500-1000 *Listeria* CFU/mL after a 2 h incubation. Following an enrichment step however, the phage could detect as few as 1 *Listeria* cell per gram of artificially contaminated salad.

Figure 23:
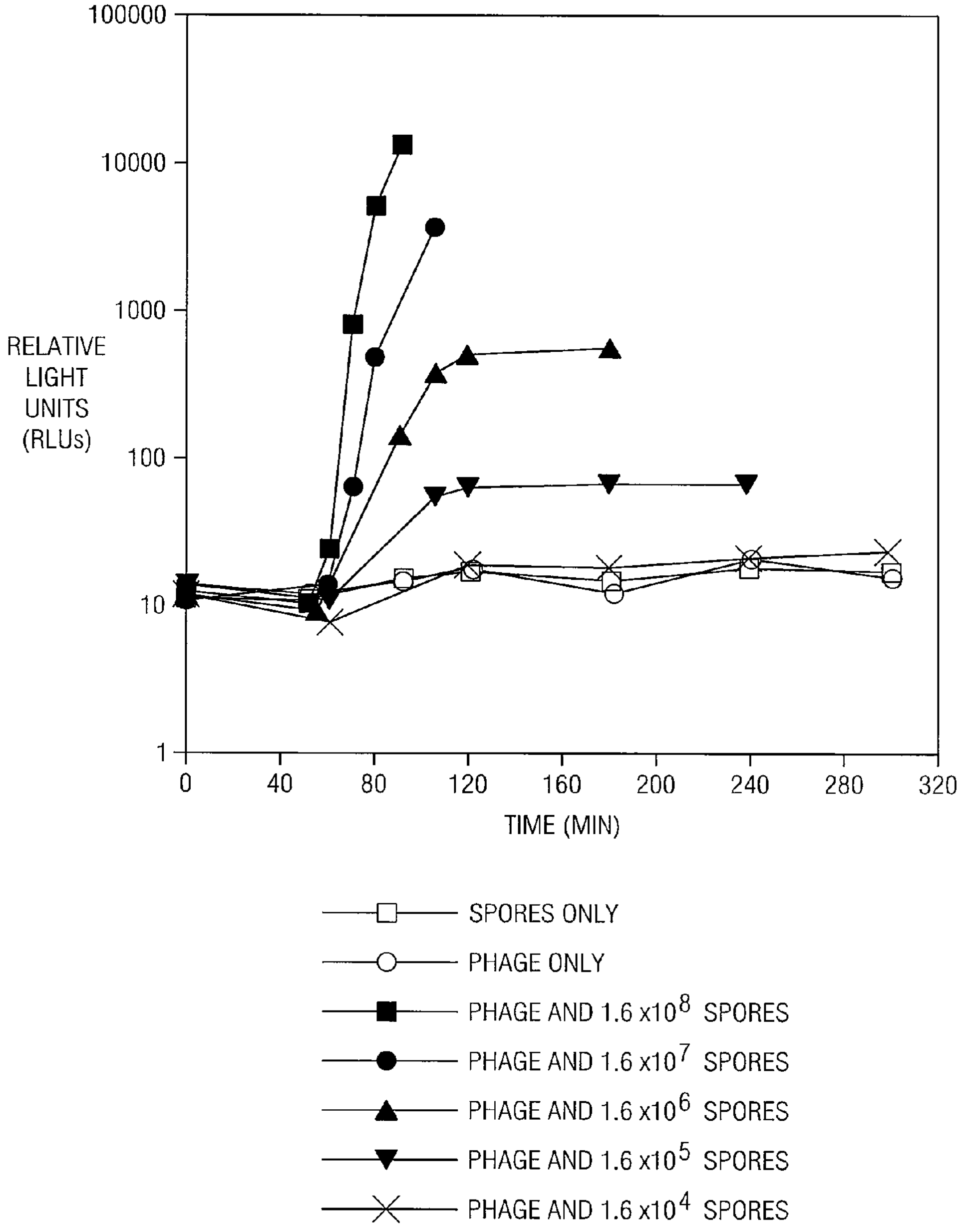
FIG. 23 shows a plot of bioluminescence (relative light units) over time observed for Wβ::luxAB-infected *B. anthracis* various dilutions of germinating spores in accordance with an embodiment of the disclosure.

To investigate assay sensitivity and dose-dependent characteristics, ten-fold serial dilutions of spores ranging from $1.6\times10^8$ to $1.6\times10^4$ CFU/mL were mixed with Wβ::luxAB phage ($4.8\times10^5$ PFU/M1) and incubated under germination inducing conditions as described above (e.g., BHI/L-alanine, 35° C.). The results demonstrated that as the number of spores decreased, bioluminescence decreased proportionally indicating dose-response characteristics (FIG. 23). As the number of spores decreased, the signal response time also decreased. Nevertheless, $1.6\times10^5$ CFU/mL resulted in a bioluminescent signal within 120 min post infection.

The sensitivity of the assay is dependent on the efficiency of infection, expression of the luxAB expression cassette, and the sensitivity of the luminometer. Assays were performed using the Biotek Synergy II multiplate detection reader whose primary modes of function are fluorescence and absorbance, with luminescence being a secondary function. Consequently, the sensitivity of the assay may be limited by the detection device. Upon further assay improvement (by increasing luxAB expression, and by increasing number of phage/assay) and a more sensitive photon detection device, a phage detection system that can detect less than 100 CFU/mL is anticipated.

As will be understood by those skilled in the art, other equivalent or alternative methods, devices, systems and compositions for detecting the presence of a target molecule and/or target microorganism according to embodiments of the present disclosure may be envisioned without departing from the essential characteristics thereof. For example, where a range is disclosed, the end points may be regarded as guides rather than strict limits. In some embodiments, methods, compositions, devices, and/or systems may be adapted to accommodate ergonomic interests, aesthetic interests, scale, or any other interests. Such modifications may influence other steps, structures and/or functions (e.g., positively, negatively, or insubstantially). A negative influence on function may include, for example, a loss of fractionation capacity and/or resolution. Yet, this loss may be deemed acceptable, for example, in view of offsetting ergonomic, aesthetic, scale, cost, or other factors.

In some embodiments, a device of the disclosure may be manufactured in either a handheld or a tabletop configuration, and may be operated sporadically, intermittently, and/or continuously. Individuals skilled in the art would recognize that additional separation methods may be incorporated, e.g., to partially or completely remove proteins, lipids, carbohydrates, nucleic acids, salts, solvents, detergents, and/or other materials from a test sample. Also, the temperature, pressure, and acceleration (e.g., spin columns) at which each step is performed may be varied.

All or part of a system of the disclosure may be configured to be disposable and/or reusable. From time to time, it may be desirable to clean, repair, and/or refurbish at least a portion of a device and/or system of the disclosure. For example, a reusable component may be cleaned to inactivate, remove, and/or destroy one or more contaminants. Individuals skilled in the art would recognize that a cleaned, repaired, and/or refurbished component is within the scope of the disclosure. In addition, individuals skilled in the art would recognize that a fractionator may further comprise an elution detector (e.g., an optical, spectrophotometric, fluorescence, and/or radioisotope detector) configured to monitor removal (e.g., elution) of phage from the binder.

These equivalents and alternatives along with obvious changes and modifications are intended to be included within the scope of the present disclosure. Moreover, one of ordinary skill in the art will appreciate that no embodiment, use, and/or advantage is intended to universally control or exclude other embodiments, uses, and/or advantages. Expressions of certainty (e.g., "will," "are," and "can not") may refer to one or a few example embodiments without necessarily referring to all embodiments of the disclosure. Accordingly, the foregoing disclosure is intended to be illustrative, but not limiting, of the scope of the disclosure.

The invention claimed is:

1. A kit comprising:

a genetically engineered lysogenic Wβ phage operable to infect a *Bacillus* microorganism and comprising a reporter nucleic acid comprising at least one luxAB gene; wherein the reporter nucleic acid comprising at least one luxAB gene is integrated into the genome of the genetically engineered lysogenic Wβ phage at a locus selected from the wp39 locus, the wp40 locus, and the wp41 locus such that a portion of the phage genome is replaced by the reporter nucleic acid; and a detector to detect expression of the luxAB gene in the infected *Bacillus* microorganism.

2. A kit according to claim 1, further comprising a luxAB substrate.

3. A kit according to claim 1, wherein the detector comprises a portable light sensor device.

4. A kit according to claim 3, wherein the portable light sensor device is automated.

5. A kit according to claim 1, configured to detect less than about five hundred eluted phage.

6. A kit according to claim 1, configured to detect less than about five eluted phage.

7. A kit according to claim 1, configured to detect about 1,000 Colony Forming Units per milliliter.

8. A kit according to claim 1, the genetically engineered lysogenic phage further comprising an expression control sequence operably linked to the reporter nucleic acid.

9. A kit according to claim 8, the expression control sequence comprising a repressible promoter.

10. A kit according to claim 1, wherein expression of the luxAB gene is detectable by the detector within one hour of infection of the *Bacillus* microorganism.

11. A kit according to claim 1, wherein the *Bacillus* microorganism is *Bacillus anthracis*, a spore or genetic variant thereof.

12. A kit according to claim 1, wherein the *Bacillus* microorganism is a *Bacillus anthracis*, a *Bacillus cereus*, a *Bacillus megaterium*, a *Bacillus pumilis*, a *Bacillus firmus*, a *Bacillus subtilis*, a *Bacillus coagulans*, a *Bacillus licheniformis*, a *Bacillus circulans*, a spore or a genetic variant thereof.

13. The kit according to claim 1, further comprising at least one container configured and arranged to contain the phage and to allow the phage to be contacted with a test sample.

14. A kit according to claim 13, wherein the test sample is taken from a patient.

15. A kit according to claim 14, wherein the patient is suspected of suffering from anthrax disease.

16. A kit according to claim 13, wherein the test sample is taken from an animal.

17. A kit according to claim 16, wherein the animal is suspected of suffering from anthrax disease.

18. A kit according to claim 13, wherein the test sample is taken from food.

19. A kit according to claim 13, wherein the test sample is taken from an environmental source.

20. A kit according to claim 19, wherein the test sample is taken from a water supply.

21. A kit according to claim 1, configured to detect expression of the luxAB gene only in viable *Bacillus* microorganisms.

22. A kit according to claim 1, wherein the phage is configured to infect both rough and smooth *Bacillus* microorganisms.

23. A kit according to claim 22, wherein the phage further comprises a modified tail fiber Wp14 protein.

24. A kit according to claim 1, wherein the reporter nucleic acid further comprises a promoter specific to the *Bacillus* microorganism and fused to the luxAB gene.

25. A kit according to claim 1, the kit being configured to be portable.

26. A kit according to claim 1, configured to detect about $1.6\times10^5$ Colony Forming Units per milliliter.

27. A kit according to claim 1, wherein the reporter nucleic acid comprising at least one luxAB gene is inserted into the genome of the genetically engineered lysogenic Wβ phage by replacement of a portion of the lysogenic Wβ phage genome by homologous recombination based on a double cross over event.

28. The kit according to claim 27, wherein the reporter nucleic acid comprising at least one luxAB gene is inserted into the genome of the genetically engineered lysogenic Wβ phage at the wp40 and wp41 loci.

* * * * *

SEQUENCE LISTING

<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: Clostridium Botulinum

<400> SEQUENCE: 1

Trp His Lys Ala Pro Arg Ala Pro Ala Pro Leu Leu
1 5 10

<210> SEQ ID NO 2
<211> LENGTH: 18
<212> TYPE: DNA
<213> ORGANISM: Artificial Sequence
<220> FEATURE:
<223> OTHER INFORMATION: E. Coli

<400> SEQUENCE: 2
taaggaggta aaaaaatg 18

<210> SEQ ID NO 3
<211> LENGTH: 20
<212> TYPE: DNA
<213> ORGANISM: Artificial Sequence -continued

```
<220> FEATURE:
<223> OTHER INFORMATION: Bacillus Subtilis
<221> NAME/KEY: "n" nucleotide
<222> LOCATION: (14)
<223> OTHER INFORMATION: "n" represents single nucleotide

<400> SEQUENCE: 3

aaaaattgac atgntataat                                           20


<210> SEQ ID NO 4
<211> LENGTH: 6
<212> TYPE: DNA
<213> ORGANISM: Artificial Sequence
<220> FEATURE:
<223> OTHER INFORMATION: Bacillus Subtilis

<400> SEQUENCE: 4

ttgaca                                                           6


<210> SEQ ID NO 5
<211> LENGTH: 6
<212> TYPE: DNA
<213> ORGANISM: Artificial Sequence
<220> FEATURE:
<223> OTHER INFORMATION: Bacillus Subtilis

<400> SEQUENCE: 5

tataat                                                           6


<210> SEQ ID NO 6
<211> LENGTH: 2
<212> TYPE: DNA
<213> ORGANISM: Artificial Sequence
<220> FEATURE:
<223> OTHER INFORMATION: Bacillus Subtilis

<400> SEQUENCE: 6

tg                                                               2
```